United States Patent
Xie et al.

(10) Patent No.: US 9,260,391 B2
(45) Date of Patent: Feb. 16, 2016

(54) HYPOGLYCEMIC DIHYDROPYRIDONES

(75) Inventors: Yuli Xie, Shanghai (CN); Shixian Deng, White Plains, NY (US); Donald W. Landry, New York, NY (US); Paul Harris, New York, NY (US); Antonella Maffei, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 838 days.

(21) Appl. No.: 13/058,142

(22) PCT Filed: Aug. 7, 2009

(86) PCT No.: PCT/US2009/004551
§ 371 (c)(1),
(2), (4) Date: Aug. 5, 2011

(87) PCT Pub. No.: WO2010/016939
PCT Pub. Date: Feb. 11, 2010

(65) Prior Publication Data
US 2011/0294800 A1   Dec. 1, 2011

Related U.S. Application Data

(60) Provisional application No. 61/188,419, filed on Aug. 8, 2008.

(51) Int. Cl.
*A61K 31/45* (2006.01)
*A61K 31/351* (2006.01)
(Continued)

(52) U.S. Cl.
CPC ............ *C07D 211/94* (2013.01); *C07D 211/76* (2013.01); *C07D 211/88* (2013.01); *C07D 309/32* (2013.01); *C07D 471/04* (2013.01)

(58) Field of Classification Search
CPC ... A61K 31/45; A61K 31/351; C07D 211/74; C07D 309/30
USPC .......... 546/243; 544/106; 549/416; 514/345, 514/460
See application file for complete search history.

(56) References Cited

U.S. PATENT DOCUMENTS 6,649,604 B2 * 11/2003 Spohr et al. .............. 514/214.02
2010/0204258 A1   8/2010 Harris et al.

FOREIGN PATENT DOCUMENTS

WO   WO 2008/112278   8/2009

OTHER PUBLICATIONS

Xie et al., Novel hypoglycemic dihydropyridones serendipitously discovered from O- versus C- alkylation in the synthesis of VMAT2 antagonist. Bioorg. Med. Chem. Lett., pp. 5111-5114 (Sep. 15, 2008).*

(Continued)

*Primary Examiner* — Kamal Saeed
*Assistant Examiner* — Janet L Coppins
(74) *Attorney, Agent, or Firm* — Bryan Cave LLP

(57) ABSTRACT

The present invention provides, inter alia, a compound of formula I: wherein the substituent designations are indicated in the Specification. The present invention also provides pharmaceutical compositions comprising a compound of formula I, and methods of treatment or prevention of diabetes or hyperglycemia in a patient, and of normalizing blood glucose levels in a subject, by administering an effective amount of a compound of formula I.

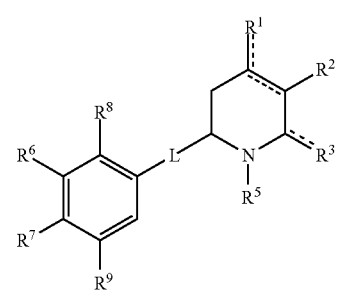

65 Claims, 16 Drawing Sheets
(3 of 16 Drawing Sheet(s) Filed in Color)

(51) Int. Cl.
*C07D 211/74* (2006.01)
*C07D 309/30* (2006.01)
*C07D 211/94* (2006.01)
*C07D 211/76* (2006.01)
*C07D 211/88* (2006.01)
*C07D 309/32* (2006.01)
*C07D 471/04* (2006.01)

(56) References Cited

OTHER PUBLICATIONS de Souza et al, Bioorganic & Medicinal Chemistry Letters 12 (2004), pp. 865-869.*
Kappe et al, 1968, pp. 85-88.*
Lundquist I et al., "Monoamines in pancreatic islets of guinea pig, hamster, rat, and mouse determined by high performance liquid chromatography," Pancreas 4:662-667 (1989).
Maffei A et al., "Identification of tissue-restricted transcripts in human islets," Endocrinology 145:4513-4521 (2004).
Mahony C et al., "Species variation in pancreatic islet monoamine uptake and action," Diabetes 26:257-261 (1977).
Murthy R et al., "Whole body [11C]-dihydrotetrabenazine imaging of baboons: biodistribution and human radiation dosimetry estimates", Eur J Nucl Med Mol Imaging, 2008, 35, 790-797.
Natalucci S et al., "Age-related analysis of glucose metabolism in spontaneously hypertensive and normotensive rats," Exp Physiol 88:399-404 (2003).
Nogueira CR, "Modulation of insulin secretion and 45Ca2+ efflux by dopamine in glucose-stimulated pancreatic islets," Gen Pharmacol 25:909-916 (1994).
Pettibone DJ, "Tetrabenazine-induced depletion of brain monoamines: characterization and interaction with selected antidepressants," Eur J Pharmacol 102:425-430 (1984).
Quinn GP et al., "Biochemical and pharmacological studies of RO 1-9569 (tetrabenazine), a nonindole tranquilizing agent with reserpine-like effects," J Pharmacol Exp Ther 127:103-109 (1959).
Raffo A. et al., "Role of vesicular monoamine transporter type 2 in rodent insulin secretion and glucose metabolism revealed by its specific antagonist tetrabenazine", J of Endocrinol, 2008, 198, 41-49.
Rosati G et al., "Effects of long-term L-dopa therapy on carbohydrate metabolism in patients with Parkinson's disease," European Neurology 14:229-239 (1976).
Rubi B et al., "Dopamine D2-like receptors are expressed in pancreatic beta cells and mediate inhibition of insulin secretion," J Biol Chem 280:36824-36832 (2005).
Scherman D, "Dihydrotetrabenazine binding and monoamine uptake in mouse brain regions," J Neurochem 47:331-339 (1986).
Scherman D et al., "Acido-basic properties of the catecholamine uptake inhibitors tetrabenazine and dihydrotetrabenazine," Biochimie 64:915-921 (1982).
Scherman D et al., "Characterization of the monoamine carrier of chromaffin granule membrane by binding of [2-3H] dihydrotetrabenazine," Proc Natl Acad Sci USA 80:584-588 (1983).
Scherman D et al., "Reserpine binding to bovine chromaffin granule membranes. Characterization and comparison with dihydrotetrabenazine binding," Mol Pharmacol 25:113122 (1984).
Shankar E et al., "Dopaminergic regulation of glucose-induced insulin secretion through dopamine 02 receptors in the pancreatic islets in vitro," IUBMB Life 58:57-163 (2006).
Shapiro A.M.J. et al., "Islet preparation in seven patients with type I diabetes mellitus using a glucocortoid-free immunosuppressive regimen", New England Journal of Medicine, 2000, 343(4), 230-238.
Sharp GW, "Mechanisms of inhibition of insulin release," Am J Physiol 271: C1781-1799 (1996).
Souza F et al., "Current progress in non-invasive imaging of beta cell mass of the endocrine pancreas," Curr Med Chem 13:2761-2773 (2006).
Souza F. et al., "Longitudinal noninvasive PET-based β cell mass estimates in a spontaneous diabetes rat model", J Clin Invest., 2006, 116(6), 1506-1513.
Squires PE et al., "Co-ordinated Ca(2+)-signalling within pancreatic islets: does beta-cell entrainment require a secreted messenger," Cell Calcium 31 :209-219 (2002).
Storto M et al., "Insulin secretion is controlled by mGlu5 metabotropic glutamate receptors," Mol Pharmacol 69: 1234-1241 (2006).
Taylor AW, "Free fatty acid levels in exercised and nonexercised reserpinized rats," Am J Physiol 223:319-322 (1972).
Uehara S et al., "Metabotropic glutamate receptor type 4 is involved in autoinhibitory cascade for glucagon secretion by alpha-cells of islet of Langerhans," Diabetes 53:998-1006 (2004).
Varoqui H et al., "Vesicular neurotransmitter transporters. Potential sites for the regulation of synaptic function," Mol Neurobiol 15:165-191 (1997).
Wang Y et al., "G;ucagon-like peptide-1 can reverse the age-related decline in glucose tolerance in rats," J Clin Invest 99:2883-2889 (1997).
Watanabe T et al., "Immunohistochemical colocalization of insulin, aromatic L-amino acid decarboxylase and dopamine beta-hydroxylase in islet B cells of chicken pancreas," Cell Tissue Res 263:131-136 (1991).
Weksler-Zangen S et al., "The newly inbred cohen diabetic rat: a nonobese normolipidemic genetic model of diet-induced type 2 diabetes expressing sex differences," Diabetes 50:2521-2529 (2001).
Wilson JP et al., "Beta cell monoamines: further evidence for their role in modulating insulin secretion," Am J Physiol 227:305-312 (1974).
Yamada H et al., "Ca2+-dependent exocytosis of L-glutamate by αTC6, clonal mouse pancreatic α-cells," Diabetes 50:1012-1020 (2001).
Zern RT et al., "Effect of increased pancreatic islet norepinephrine, dopamine and serotonin concentration on insulin secretion in the golden hamster" Diabetologia 18:341-346 (1980).
Zheng G et al., "Vesicular Monoamine Transporter 2: Role as a Novel Target for Drug Development", AAPS J., 8(4), E682-692, (2006).
Adeghate E et al., "Distribution of acetylcholinesterase-and monoamine oxidase-positive neurons in pancreatic tissue transplant," Acta Histochem 89: 183-186 (1990).
Adeghate E et al., "Dopamine-beta-hydroxylase-positive nerves in normal and transplanted pancreatic tissue in the anterior eye-chamber of rats," J Chem Neuroanat 4:223-227 (1991).
AFT Pharmaceuticals. Datasheet Xenazine 25. [online] Available on the internet at <<http://www.medsafe.govt.nz/profs/datasheet/x/Xenazine25tab.pdf>> Prepared on Sep. 12, 2006 [retrieved on Mar. 29, 2012].
Ahrén B, "Autonomic regulation of islet hormone secretion—implications for health and disease," Diabetologia 43:393-410 (2000).
Ahrén B et al., Neuropeptidergic versus cholinergic and adrenergic regulation of islet hormone secretion. Diabetologia 29:827-836 (1986).
Ahrén B et al,, "Effects of L-dopa-induced dopamine accumulation on 45Ca2+ efflux and insulin secretion in isolated rat islets," Pharmacology 30:71-82 (1985).
Ahrén B et al,, "Influence of the sympatho-adrenal system and somatostatin on the secretion of insulin in the rat," J Physiol 312:563-575 (1981).
Aleyassine H et al., "Dual action of antidepressant drugs (MAO inhibitors) on insulin release," Endocrinology 96:702-710 (1975).
Anlauf M. et al., "Expression of the Two Isoforms of the Vesicular Monoamine Transporter (VMAT1 and VMAT2) in the Endocrine Pancreas and Pancreatic Endocrine Tumors", J Histochem Cytochem., 2003, 51(8), 1027-1040.
Arneric SP et al., "Dopamine analog-induced hyperglycemia in rats: involvement of the adrenal medulla and the endocrine pancreas," J Pharmacol Exp Ther 228:551-559 (1984).
Arneric SP et al., "Inhibition of insulin release from rat pancreatic islets by drugs that are analogues of dopamine," Diabetes 33:888-893 (1984).
Barker CJ et al., "Phosphorylated inositol compounds in beta-cell stimulus-response coupling," Am J Physiol Endocrinol Metab 283:E1113-1122 (2002).
Bird JL et al., "Pancreatic islets: a tissue rich in serotonin," Diabetes 29:304-308 (1980).

(56) References Cited

OTHER PUBLICATIONS

Borelli MI et al., "Possible modulatory effect of endogenous islet catecholamines on insulin secretion," BMC Endocr Disord 1:1 (2001).
Borelli MI et al., "Presence of DOPA decarboxylase and its localisation in adult rat pancreatic islet cells," Diabetes Metab 23:161-163 (1997).
Borelli MI et al., "Tyrosine hydroxylase activity in the endocrine pancreas: changes induced by short-term dietary manipulation," BMC Endocr Disord 3:2 (2003).
Brice NL et al., "Metabotropic glutamate and GABA(B) receptors contribute to the modulation of glucose-stimulated insulin secretion in pancreatic beta cells," Diabetologia 45:242-252 (2002).
Brodoff BN et al., "Biogenic-Amines and Diabetes in Sand Rat," Hormone and Metabolic Research 4:310 (1972).
Brunicardi FC et al., "Neural regulation of the endocrine pancreas," Int J Pancreatol 18:177-195 (1995).
Cegrell L "The occurrence of biogenic monoamines in the mammalian endocrine pancreas," Acta Physiol Scand Suppl 314: 1-60 (1968).
Cegrell L et al., "Dopamine and 5-hydroxytryptamine in the guinea-pig pancreas," Life Sci 6:2483-2489 (1967).
Cetin Y "Biogenic amines in the guinea pig endocrine pancreas," Life Sci 50:1343-1350 (1992).
Duttaroy A et al., "Muscarinic stimulation of pancreatic insulin and glucagon release is abolished in m3 muscarinic acetylcholine receptordeficient mice," Diabetes 53:1714-1720 (2004).
Eiden LE et al., "The vesicular amine transporter family (SLC18): amine/proton antiporters required for vesicular accumulation and regulated exocytotic secretion of monoamines and acetylcholine," Pflugers Arch 447:636-640 (2004).
El-Mansoury AM et al., "Activation of protein kinase C modulates alpha2-adrenergic signalling in rat pancreatic islets," Cell Signal 10:637-643 (1998).
Ekholm R et al., "Monoamines in the pancreatic islets of the mouse. Subcellular localization of 5-hydroxytryptamine by electron microscopic autoradiography" Diabetologia 7:339-348 (1971).
Erickson JD et al., "Distinct pharmacological properties and distribution in neurons and endocrine cells of two isoforms of the human vesicular monoamine transporter," Proc Natl Acad Sci USA 93:5166-5171 (1996).
Ericson et al., "Accumulation of Dopamine in Mouse Pancreatic B-Cells Following Injection of L-DOPA Localization to Secretory Granules and Inhibition of Insulin Secretion," Diabetologia, 13(2), pp. 117-124 (1977).
Feldman JM et al., "Characterization of pancreatic islet monoamine oxidase," Metabolism 24:581-588 (1975).
Feldman JM et al., "Monoamine oxidase inhibitors: nature of their interaction with rabbit pancreatic islets to alter insulin secretion," Diabetologia 11 :487-494 (1975).
Gilon P. et al., "Mechanisms and physiological significance of the cholinergic control of pancreatic beta-cell function," Endocr Rev 22:565-604 (2001).

Hansen SE et al., "Simultaneous determination of the content of serotonin, dopamine, noradrenaline and adrenaline in pancreatic islets isolated from fed and starved mice," Acta Endocrinol (Copenh) 86:820-832 (1977).
Hayashi M et al., "Secretory granule-mediated co-secretion of L-glutamate and glucagon triggers glutamatergic signal transmission in islets of Langerhans," J Biol Chem 278:1966-1974 (2003).
Henquin JC, "Triggering and amplifying pathways of regulation of insulin secretion by glucose," Diabetes 49:1751-1760 (2000).
Howell M et al., "Cloning and functional expression of a tetrabenazine sensitive vesicular monoamine transporter from bovine chromaffin granules," FEBS Lett 338:16-22 (1994).
Høy M et al., "Increase in cellular glutamate levels stimulates exocytosis in pancreatic beta-cells," FEBS Lett 531: 199-203 (2002).
Iturriza FC et al., "Immunohistochemical investigation of tyrosine-hydroxylase in the islets of Langerhans of adult mice, rats and guinea pigs," Neuroendocrinology 57:476-480 (1993).
Jaim-Etcheverry G et al., "Electron microscopic cytochemistry of 5-hydroxytryptamine (5-HT) in the beta cells of guinea pig endocrine pancreas," Endocrinology 83:917-923 (1968).
Kenney C et al., "Tetrabenazine in the treatment of hyperkinetic movement disorders," Expert Rev Neurother 6:7-17 (2006).
Kitamura N. et al., "An immunohistochemical survey of catecholamine-synthesizing enzyme-immunoreactive nerves and endocrine cells in the bovine pancreas," Anat Histol Embryol 28:81-84 (1999).
Koeppe et al., "11C-DTBZ and 18F-FDG PET Measures in Differentiating Dementias," J Nuclear Medicine 46:936-944 (2005).
Lake SP et al., "Large-scale purification of human islets utilizing discontinuous albumin gradient on IBM 2991 cell separator," Diabetes 38 Suppl 1 :143-145 (1989).
Lakey JR et al., "Intraductal collagenase delivery into the human pancreas using syringe loading or controlled perfusion," Cell Transplant 8:285-292 (1999).
Lakey JR et al., "Variables in organ donors that affect the recovery of human islets of Langerhans," Transplantation 61 :1047-1053 (1996).
Lane JD et al., "Neurochemical changes following the administration of depleters of biogenic monoamines," Life Sci 19:1663-1667 (1976).
Lenzen S et al., "Monoamine oxidase in pancreatic islets, exocrine pancreas, and liver from rats. Characterization with clorgyline, deprenyl, pargyline, tranylcypromine, and amezinium," Naunyn Schmiedebergs Arch Pharmacol 324:190-195 (1983).
Liu Y et al., "The role of vesicular transport proteins in synaptic transmission and neural degeneration," Annu Rev Neurosci 20:125-156 (1997).
Livak KJ et al., "Analysis of relative gene expression data using real-time quantitative PCR and the 2(-Delta Delta C (T)) Method," Methods 25:402-408 (2001).
Lübbers T et al., "1,3-Disubstituted 4-aminopiperidines as useful tools in the optimization of the 2-aminobenzo[a] quinolizine dipeptidyl peptidase IV inhibitors", Biorg Med Chem Lett., 2007, 17, 2966-2970.
Lundquist I, "Insulin secretion. Its regulation by monoamines and acid amyloglucosidase," Acta Physiol Scand Suppl 372:1-47 (1971).

* cited by examiner

Synthetic Scheme for Compound 6

Alternative Synthetic Scheme

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: synthetic construct; Cyclophilin A-5'

<400> SEQUENCE: 1
cttcgacatc acggctgatg g                                              21

<210> SEQ ID NO 2
<211> LENGTH: 20
<212> TYPE: DNA
<213> ORGANISM: Artificial
<220> FEATURE:
<223> OTHER INFORMATION: synthetic construct; Cyclophilin A-3'

<400> SEQUENCE: 2
caggacctgt atgcttcagg                                                20

<210> SEQ ID NO 3
<211> LENGTH: 20
<212> TYPE: DNA
<213> ORGANISM: Artificial
<220> FEATURE:
<223> OTHER INFORMATION: synthetic construct; VMAT2-5'

<400> SEQUENCE: 3
gccctgccca tctggatgat                                                20

<210> SEQ ID NO 4
<211> LENGTH: 23
<212> TYPE: DNA
<213> ORGANISM: Artificial
<220> FEATURE:
<223> OTHER INFORMATION: synthetic construct; VMAT2-3'

<400> SEQUENCE: 4
ctttgcaata gcaccaccag cag                                            23

<210> SEQ ID NO 5
<211> LENGTH: 18
<212> TYPE: DNA
<213> ORGANISM: Artificial
<220> FEATURE:
<223> OTHER INFORMATION: synthetic construct; rINS1/2-5'

<400> SEQUENCE: 5
cccaggcttt tgtcaaac                                                  18

<210> SEQ ID NO 6
<211> LENGTH: 18
<212> TYPE: DNA
<213> ORGANISM: Artificial
<220> FEATURE:
<223> OTHER INFORMATION: synthetic construct; rINS1/2-3'

<400> SEQUENCE: 6
cttgcgggtc ctccactt                                                  18
```

HYPOGLYCEMIC DIHYDROPYRIDONES

CROSS-REFERENCE TO RELATED APPLICATIONS

The present application is a U.S. National Stage Application of International Application No. PCT/US2009/004551, which was filed on Aug. 7, 2009, which claims priority to U.S. Provisional Patent Application Ser. No. 61/188,419, filed Aug. 8, 2008, the entire contents of which are incorporated by reference in their entirety as if recited in full herein.

INCORPORATION BY REFERENCE OF SEQUENCE LISTING

This application contains references to amino acids and/or nucleic acid sequences that have been filed concurrently herewith as sequence listing text file "IR2358_0235603_Sequence_Listing_ST25.txt", file size of 1.41 KB, created on Dec. 23, 2010. The aforementioned sequence listing is hereby incorporated by reference in its entirety pursuant to 37 C.F.R. §1.52(e)(5).

FIELD OF THE INVENTION

The field of the present invention relates to dihydropyridone compounds and compositions, as well as methods for use thereof for treating, preventing or ameliorating the effects of diabetes or hyperglycemia, and for normalizing blood glucose levels.

BACKGROUND OF THE INVENTION

D-Glucose, often in combination with certain amino acids, is the major physiological stimuli for insulin secretion. Net insulin production and glucose homeostasis, however, is regulated by a number of other substances, including several neurotransmitters that act directly on β-cells and indirectly through other target tissues. Many of these substances function as amplifying agents that have little or no effect by themselves, but enhance the signals triggered by the β-cell glucose sensing apparatus.

For example, during the cephalic phase of digestion, acetylcholine (ACh) is released via parasympathetic nerve terminals ending in islets. β-cells express the M3 muscarinic receptor and respond to exogenous ACh with increased inositol phosphate production, which in turn facilitates $Na^+$ ion exit and calcium ion entry. This results in augmented insulin vesicle exocytosis. The amino acid glutamate, the major excitatory neurotransmitter in the central nervous system, can be found in both α- and β-cells of the endocrine pancreas. It is stored in glucagon- or insulin-containing granules, and appears to enhance insulin secretion when it is released. The presence of metabotropic glutamate receptors on α- and β-cells themselves suggests the presence of both autocrine and paracrine circuits within islet tissue involved in the regulation of insulin secretion.

Other neurotransmitters, such as the monoamines epinephrine and norepinephrine, released in circulation, may act to suppress glucose-stimulated insulin secretion by direct interaction with adrenoreceptors expressed (mainly the α-2 receptor) on pancreatic β-cells. β-cells of the endocrine pancreas also express dopamine receptors (D2) and respond to exogenous dopamine with inhibited glucose-stimulated insulin secretion. Purified islet tissue itself is a rich source of monoamines, and has been shown to contain 5-hydroxytryptamine, epinephrine, norepinephrine and dopamine.

β-cells also have the biosynthetic apparatus to create, dispose of, and store specific neurotransmitters. For example, islet tissue has been shown to include (a) tyrosine hydroxylase, the enzyme responsible for catalyzing the conversion of L-tyrosine to dihydroxyphenylalanine (DOPA), a precursor of dopamine, (b) L-DOPA decarboxylase, responsible for converting L-DOPA to dopamine, and (c) dopamine β-hydroxylase, the enzyme that catalyzes the conversion of dopamine to norepinephrine.

In addition, L-3,4-dihydroxyphenylalanine (L-DOPA) is rapidly converted to dopamine in islet β-cells. Monoamine oxidase (MAO) is a catabolic enzyme responsible for the oxidative de-amination of monoamines, such as dopamine and catecholamines, and maintains the homeostasis of monoamine-containing synaptic vesicles. The possible role of MAO in islet function has been studied, and MAO has been detected in the large majority of pancreatic islet cells, including β-cells. Interestingly, some MAO inhibitors have been shown to antagonize glucose-induced insulin secretion. The secretory granules of pancreatic β-cells have been documented to have the ability to store substantial amounts of calcium, dopamine, and serotonin therein.

In the central nervous system, the storage of monoamine neurotransmitters in secretory organelles is mediated by vesicular amine transporters. These molecules are expressed as integral membrane proteins of the lipid bilayer of secretory vesicles in neuronal and endocrine cells. By way of an electrochemical gradient, the vesicular amine transporters exchange one cytosolic monoamine, such as dopamine, for two intravesicular protons functioning to package neurotransmitters for later discharge into the synaptic space. Accordingly, vesicular monoamine transporters (VMAT) are members of the vesicular transporter family responsible for the uptake and secretion of monoamine neurotransmitters in neurons and endocrine cells. Zheng G, et al., *AAPS J.* 2006, 8(4), 689.

Two isoforms of VMAT (type 1 and 2) have been cloned, and both immunohistochemistry and gene expression studies have shown that the insulin-producing beta cells in the pancreas only express the VMAT2 isoform. Anlauf M., et al., *J Histochem Cytochem.* 2003, 51, 1027. The feasibility of noninvasive measurement of beta cell mass has been demonstrated both in humans and rodents by positron emission tomography (PET) using VMAT2 as the biomarker and its specific antagonist dihydrotetrabenazine (DTBZ) as the tracer. Souza F., et al., *J Clin Invest.* 2006, 116(6), 1506; Murthy R, et al., *Eur J Nucl Med Mol Imaging* 2008, 35(4), 790-797. Studies have shown that VMAT2 plays an important functional role in the regulation of insulin secretion in beta cells. Raffo A., et al., *J of Endocrinol* 2008, 198, 141-49. VMAT2 antagonist tetrabenazine (TBZ) and its active metabolite DTBZ are potent hypoglycemic agents that stimulate insulin secretion in vitro and improve glucose tolerance in normal and diabetic rats. Raffo A., et al., *J of Endocrinol* 2008, 198, 141-49.

Diabetes mellitus is a growing epidemic affecting hundreds of millions worldwide. Despite the existence of new classes of hypoglycemic agents, the medical need remains largely unmet and innovative therapeutics are still needed. VMAT2 antagonists have potential in the management of diabetes and hyperglycemia.

SUMMARY OF THE INVENTION

An embodiment of the present invention is a compound of formula I:

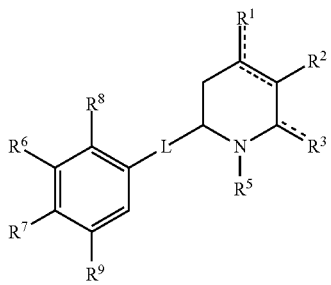

wherein
R¹ is XR⁴ or O;
R² is H or $C_1$-$C_8$ alkyl;
R³ is H or O;
X is O, S, NH or $CH_2$;
R⁴ is H or $C_1$-$C_8$ alkyl;
R⁵ is selected from the group consisting of H and $C_1$-$C_8$ alkyl, amine, $C_1$-$C_8$ alkylamine, acyl and amide;
----- is an optional double bond,
L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;
R⁶ and R⁷ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;
R⁸ and R⁹ are each independently selected from the group consisting of H, $C_1$-$C_8$ alkyl, $C_1$-$C_8$ alkoxy, amine, $C_1$-$C_8$ alkylamine, and halo; and
when one of R¹ or R³ is O, then the other is not O;
when ---- is not present between ring carbons, R² is other than H;
or an enantiomer, optical isomer, diastereomer, N-oxide, crystalline form, hydrate, or pharmaceutically acceptable salt thereof.

In another embodiment, a compound of the formula II is provided:

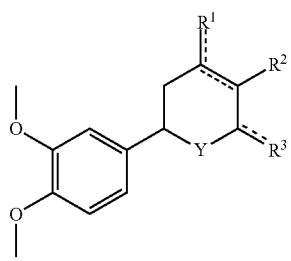

wherein
Y is NH or O;
R¹ is XR⁴ or O;
R² is H or $C_1$-$C_8$ alkyl;
R³ is H or O;
X is NH or O;
R⁴ is H, $C_1$-$C_8$ alkyl, C(═O)-heterocyclic; and
----- is an optional double bond;
or an enantiomer, optical isomer, diastereomer, N-oxide, crystalline form, hydrate, or pharmaceutically acceptable salt thereof.

Pharmaceutical compositions comprising a compound of formula I or of formula II are provided.

Methods of treatment or prevention of diabetes or hyperglycemia are provided in which a patient is administered an effective amount of a compound of formula I or II. Methods of normalizing blood glucose levels are provided in which a patient is administered an effective amount of a compound of formula I or II.

In another embodiment, a pharmaceutical composition is provided comprising a compound of formula III:

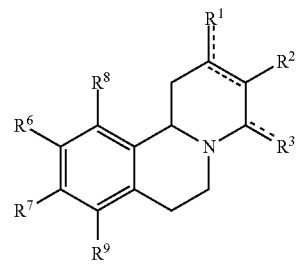

wherein
R¹ is XR⁴ or O;
R² is H or $C_1$-$C_8$ alkyl;
R³ is H or O;
X is O, S, NH or $CH_2$;
R⁴ is H, $C_1$-$C_8$ alkyl, or C(═O)-heterocyclic; and
----- is an optional double bond;
when one of R¹ or R³ is O, then the other is not O,
when ---- is not present between ring carbons, R² is other than H;
R⁶ and R⁷ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl; and
R⁸ and R⁹ are each independently selected from the group consisting of H, $C_1$-$C_8$ alkyl, $C_1$-$C_8$ alkoxy, amine, $C_1$-$C_8$ alkylamine, and halo;
with the proviso that when R² is 2-methyl propyl, R³ is H, and ---- is not present, R¹ is not OH and is not O;
or an enantiomer, optical isomer, diastereomer, N-oxide, crystalline form, hydrate, or pharmaceutically acceptable salt thereof;
and a pharmaceutically acceptable carrier.

Methods of treatment or prevention of diabetes or hyperglycemia are provided in which a patient is administered an effective amount of a compound of formula III. Methods of normalizing blood glucose levels are provided in which a patient is administered an effective amount of a compound of formula III.

BRIEF DESCRIPTION OF THE FIGURES

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
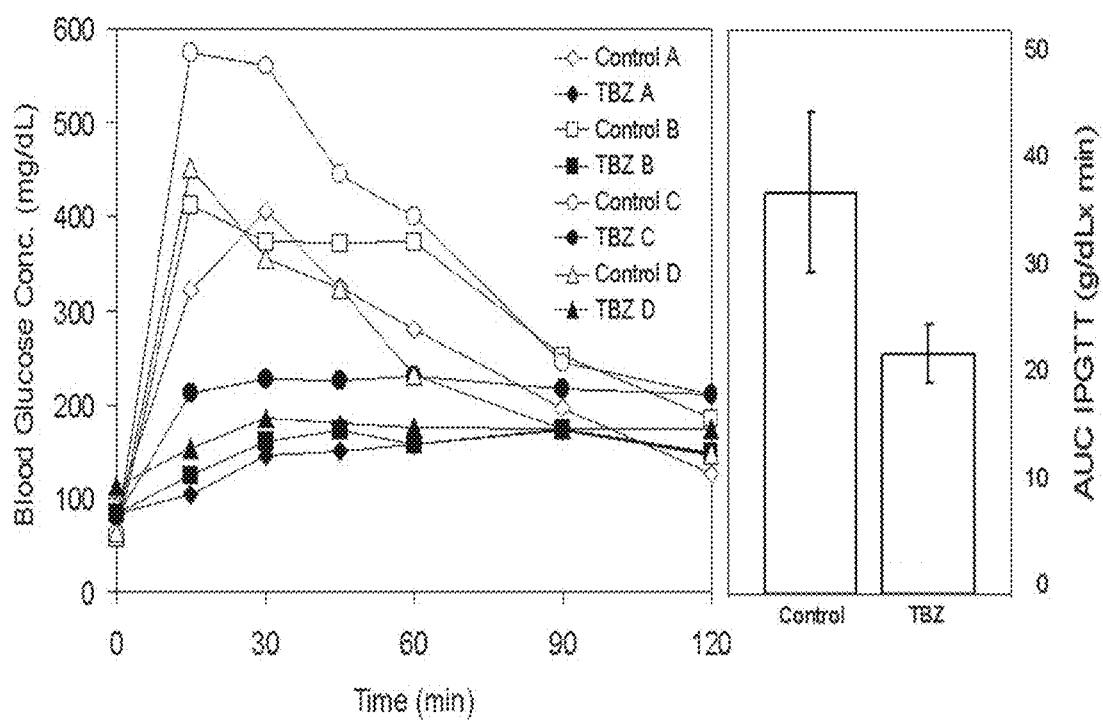
FIG. 1. Tetrabenazine (TBZ) reduces the blood glucose excursion during an intraperitoneal glucose tolerance test (IPGTT). Left panel. Blood glucose values during an IPGTT of Lewis rats (9-11 week old) treated with vehicle alone (open symbols) or with tetrabenazine (1.6 µg/gm body weight) (closed symbols). Right panel. Cumulative results from a series of experiments (n=4). The AUC (area under the curve) IPGTT for controls was significantly higher than the AUC IPGTT TBZ treated animals (p<0.05). Error bars represent the standard error of the mean.

One embodiment of the present invention is a compound of formula I:

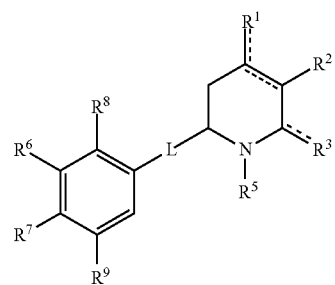

I wherein
R¹ is XR⁴ or O;
R² is H or $C_1$-$C_8$ alkyl;
R³ is H or O;
X is O, S, NH or $CH_2$;
R⁴ is H or $C_1$-$C_8$ alkyl;
R⁵ is selected from the group consisting of H and $C_1$-$C_8$ alkyl, amine, $C_1$-$C_8$ alkylamine, acyl and amide;
----- is an optional double bond,
L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;
R⁶ and R⁷ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;
R⁸ and R⁹ are each independently selected from the group consisting of H, $C_1$-$C_8$ alkyl, $C_1$-$C_8$ alkoxy, amine, $C_1$-$C_8$ alkylamine, and halo; and
when one of R¹ or R³ is O, then the other is not O;
when ---- is not present between ring carbons, R² is other than H;
or an enantiomer, optical isomer, diastereomer, N-oxide, crystalline form, hydrate, or pharmaceutically acceptable salt thereof.

An embodiment of a compound of formula I is a compound in which R¹ is XR⁴. In a further embodiment thereof, R⁴ is H or $C_1$-$C_4$ alkyl.

In another embodiment of a compound of formula I, R² is H or $C_1$-$C_4$ alkyl.

In another embodiment of a compound of formula I, X is O.

In another embodiment of a compound of formula I, L is a bond.

In another embodiment of a compound of formula I, R⁶ and R⁷ are each independently selected from the group consisting of $OCH_3$, $NH_2$, and Cl. In a further embodiment thereof, R⁶ and R⁷ are both $OCH_3$.

In another embodiment of a compound of formula I, R⁸ and R⁹ are both H.

Representative, non-limiting examples of compounds of formula I according to the present invention include compounds HG-1, HG-3, and HG-4.

HG-1

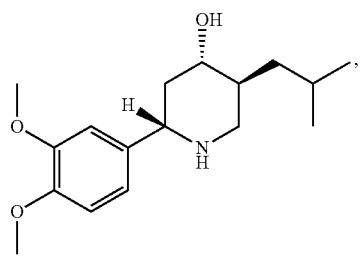

HG-3

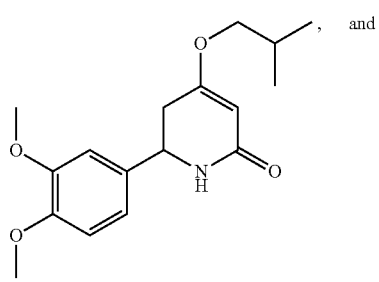, and

HG-4

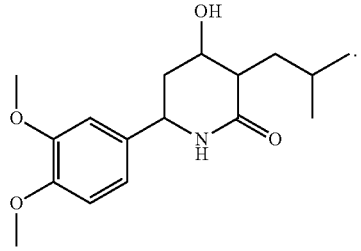

or an enantiomer, optical isomer, diastereomer, N-oxide, crystalline form, hydrate, or pharmaceutically acceptable salt thereof.

Preferred compounds thereof are compounds HG-3 and HG-4.

Pharmaceutical compositions are provided comprising a compound of formula I as above, or an enantiomer, optical isomer, diastereomer, N-oxide, crystalline form, hydrate, or pharmaceutically acceptable salt thereof; and a pharmaceutically acceptable carrier. In addition, embodiments of the invention include pharmaceutical compositions which comprise the embodiments of a compound of formula I above, including embodiments comprising compounds HG-1, HG-3, and HG-4, preferably HG-3 and/or HG-4, or an enantiomer, optical isomer, diastereomer, N-oxide, crystalline form, hydrate, or pharmaceutically acceptable salt thereof; and a pharmaceutically acceptable carrier.

Methods of treatment or prevention of diabetes or hyperglycemia are provided which comprise administering to a patient an effective amount of a compound of formula I as above, or an enantiomer, optical isomer, diastereomer, N-oxide, crystalline form, hydrate, or pharmaceutically acceptable salt thereof. In addition, embodiments of the present invention include methods of treatment or prevention of diabetes or hyperglycemia which comprise administering to a patient an effective amount of the embodiments of a compound of formula I above, including embodiments comprising HG-1, HG-3, and HG-4, preferably HG-3 and/or HG-4, or an enantiomer, optical isomer, diastereomer, N-oxide, crystalline form, hydrate, or pharmaceutically acceptable salt thereof.

Methods of normalizing blood glucose levels are provided which comprise administering to a subject an effective amount of a compound of formula I as above, or an enantiomer, optical isomer, diastereomer, N-oxide, crystalline form, hydrate, or pharmaceutically acceptable salt thereof. In addition, embodiments of the present invention include methods of normalizing blood glucose levels which comprise administering to a subject an effective amount of the embodiments of a compound of formula I above, including embodiments comprising HG-1, HG-3, and HG-4, preferably HG-3 and/or HG-4, or an enantiomer, optical isomer, diastereomer, N-oxide, crystalline form, hydrate, or pharmaceutically acceptable salt thereof.

Another embodiment of the present invention is a compound of the formula II:

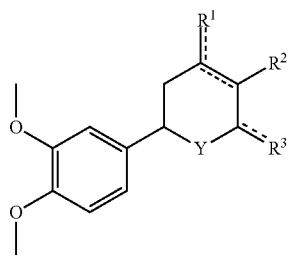

II wherein
Y is NH or O;
$R^1$ is $XR^4$ or O;
$R^2$ is H or $C_1$-$C_8$ alkyl;
$R^3$ is H or O;
X is NH or O;
$R^4$ is H, $C_1$-$C_8$ alkyl, C(=O)-heterocyclic; and
----- is an optional double bond;
or an enantiomer, optical isomer, diastereomer, N-oxide, crystalline form, hydrate, or pharmaceutically acceptable salt thereof.

An embodiment of a compound of formula II is a compound in which
Y is NH or O;
$R^1$ is $XR^4$ or O;
$R^2$ is H or $C_1$-$C_8$ alkyl;
X is O;
$R^4$ is H or $C_1$-$C_8$ alkyl; and
----- is an optional double bond.

In another embodiment of a compound of formula II, Y is NH. In a further embodiment thereof, representative, non-limiting examples of formula II are compounds selected from the group consisting of:

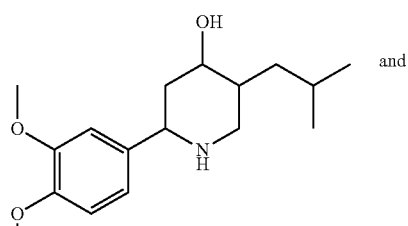

HG-2

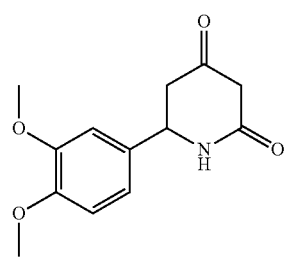

HG-5 or an enantiomer, optical isomer, diastereomer, N-oxide, crystalline form, hydrate, or pharmaceutically acceptable salt thereof.

In another embodiment of a compound of formula II, Y is O. In a further embodiment thereof, representative, non-limiting examples of formula II are compounds selected from the group consisting of:

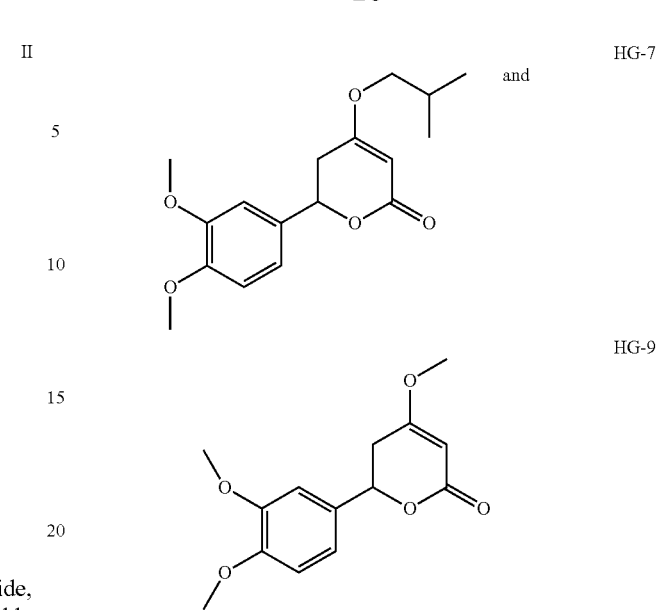

HG-7 and

HG-9 or an enantiomer, optical isomer, diastereomer, N-oxide, crystalline form, hydrate, or pharmaceutically acceptable salt thereof.

Pharmaceutical compositions are provided comprising a compound of formula II as above, or an enantiomer, optical isomer, diastereomer, N-oxide, crystalline form, hydrate, or pharmaceutically acceptable salt thereof; and a pharmaceutically acceptable carrier. In addition, embodiments of the invention include pharmaceutical compositions which comprise the embodiments of a compound of formula II above, including embodiments comprising compounds HG-2, HG-5, HG-7, and HG-9, or an enantiomer, optical isomer, diastereomer, N-oxide, crystalline form, hydrate, or pharmaceutically acceptable salt thereof; and a pharmaceutically acceptable carrier.

Methods of treatment or prevention of diabetes or hyperglycemia are provided which comprise administering to a patient an effective amount of a compound of formula II as above, or an enantiomer, optical isomer, diastereomer, N-oxide, crystalline form, hydrate, or pharmaceutically acceptable salt thereof. In addition, embodiments of the present invention include methods of treatment or prevention of diabetes or hyperglycemia which comprise administering to a patient an effective amount of the embodiments of a compound of formula II above, including embodiments comprising HG-2, HG-5, HG-7, and HG-9, or an enantiomer, optical isomer, diastereomer, N-oxide, crystalline form, hydrate, or pharmaceutically acceptable salt thereof.

Methods of normalizing blood glucose levels are provided which comprise administering to a subject an effective amount of a compound of formula II as above, or an enantiomer, optical isomer, diastereomer, N-oxide, crystalline form, hydrate, or pharmaceutically acceptable salt thereof. In addition, embodiments of the present invention include methods of normalizing blood glucose levels which comprise administering to a subject an effective amount of the embodiments of a compound of formula II above, including embodiments comprising HG-2, HG-5, HG-7, and HG-9, or an enantiomer, optical isomer, diastereomer, N-oxide, crystalline form, hydrate, or pharmaceutically acceptable salt thereof.

In another aspect of the present invention, a compound is provided which is selected from the group consisting of:

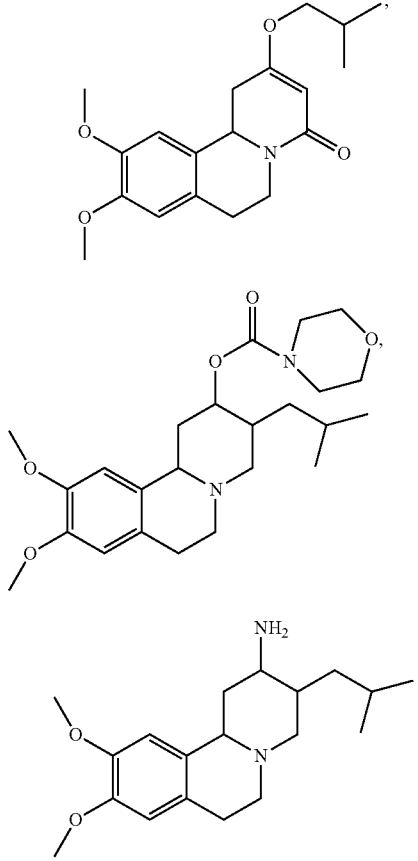

or an enantiomer, optical isomer, diastereomer, N-oxide, crystalline form, hydrate, or pharmaceutically acceptable salt thereof.

In another aspect of the present invention, a pharmaceutical composition is provided which comprises a compound which is selected from the group consisting of HG-8, HG-11, and HG-6; or an enantiomer, optical isomer, diastereomer, N-oxide, crystalline form, hydrate, or pharmaceutically acceptable salt thereof; and a pharmaceutically acceptable carrier. In a preferred embodiment, the compound in the pharmaceutical composition is HG-8 or HG-11.

In another embodiment, a method of treatment or prevention of diabetes or hyperglycemia is provided which comprises administering to a patient an effective amount of a compound selected from the group consisting of HG-8, HG-11 and HG-6, or an enantiomer, optical isomer, diastereomer, N-oxide, crystalline form, hydrate, or pharmaceutically acceptable salt thereof. In a further embodiment, a method of normalizing blood glucose levels is provided which comprises administering to a subject an effective amount of a compound selected from the group consisting of HG-8, HG-11 and HG-6, or an enantiomer, optical isomer, diastereomer, N-oxide, crystalline form, hydrate, or pharmaceutically acceptable salt thereof. In preferred embodiments, the compound administered is HG-8 or HG-11.

In a further embodiment of the present invention, a pharmaceutical composition is provided comprising a compound of formula III:

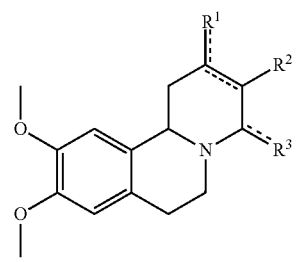

wherein
$R^1$ is $XR^4$ or O;
$R^2$ is H or $C_1$-$C_8$ alkyl;
$R^3$ is H or O;
X is O, S, NH or $CH_2$;
$R^4$ is H, $C_1$-$C_8$ alkyl, or C(=O)-heterocyclic; and
----- is an optional double bond;
when one of $R^1$ or $R^3$ is O, then the other is not O,
when ---- is not present between ring carbons, $R^2$ is other than H;
$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl; and
$R^8$ and $R^9$ are each independently selected from the group consisting of H, $C_1$-$C_8$ alkyl, $C_1$-$C_8$ alkoxy, amine, $C_1$-$C_8$ alkylamine, and halo;
with the proviso that when $R^2$ is 2-methyl propyl, $R^3$ is H, and ---- is not present, $R^1$ is not OH and is not O;
or an enantiomer, optical isomer, diastereomer, N-oxide, crystalline form, hydrate, or pharmaceutically acceptable salt thereof;
and a pharmaceutically acceptable carrier.

A preferred embodiment of a pharmaceutical composition which comprises a compound of formula III is a pharmaceutical composition comprising a compound of formula IV:

IV wherein
$R^1$, $R^2$, and $R^3$ are as defined in formula III;
X is NH or O; and
$R^4$ is H, $C_1$-$C_8$ alkyl, —C(=O)-heterocyclic;
or an enantiomer, optical isomer, diastereomer, N-oxide, crystalline form, hydrate, or pharmaceutically acceptable salt thereof;
and a pharmaceutically acceptable carrier.

Representative, non-limiting examples of compounds of formula III or IV of a pharmaceutical composition of the present invention include a compound selected from the group consisting of:

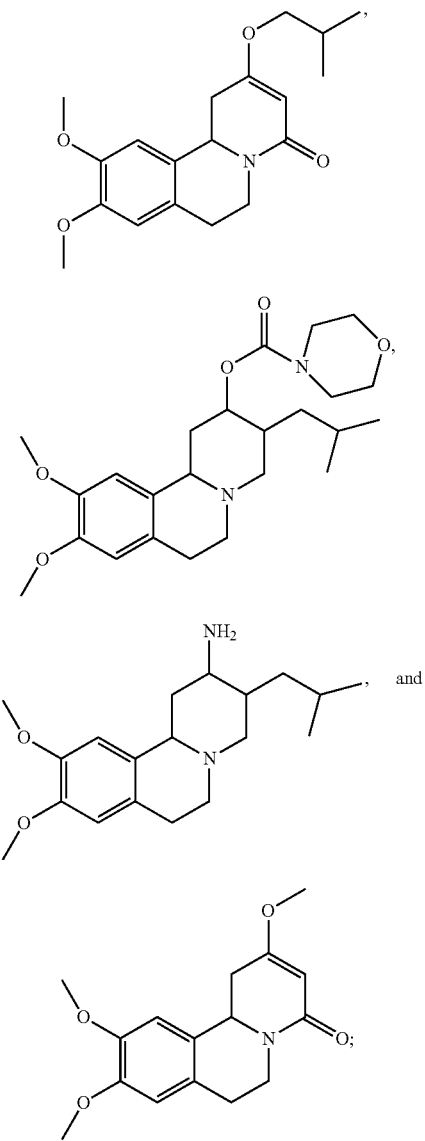

or an enantiomer, optical isomer, diastereomer, N-oxide, crystalline form, hydrate, or pharmaceutically acceptable salt thereof;
and a pharmaceutically acceptable carrier.

Methods of treatment or prevention of diabetes or hyperglycemia are provided which comprise administering to a patient an effective amount of a compound of formula III as above, or an enantiomer, optical isomer, diastereomer, N-oxide, crystalline form, hydrate, or pharmaceutically acceptable salt thereof. In a preferred embodiment, compound of formula III is a compound of formula IV as above. In addition, embodiments of the present invention include the methods using a compound selected from HG-8, HG-11, HG-6, and HG-10, or an enantiomer, optical isomer, diastereomer, N-oxide, crystalline form, hydrate, or pharmaceutically acceptable salt thereof.

Methods of normalizing blood glucose levels are provided which comprise administering to a subject an effective amount of a compound of formula III as above, or an enantiomer, optical isomer, diastereomer, N-oxide, crystalline form, hydrate, or pharmaceutically acceptable salt thereof. In a preferred embodiment, compound of formula III is a compound of formula IV as above. In addition, embodiments of the present invention include the aforementioned methods of using a compound selected particularly from HG-8, HG-11, HG-6, and HG-10.

A synthetic intermediate is also provided which is a compound of the formula:

All possible enantiomers, optical isomers, and diastomers of each formula and compound recited herein are part of the invention, whether they are explicitly shown or not. In the present invention, the isomeric forms of the compounds may be synthesized de novo. Alternatively, the specific desired isomeric form may be separated from, e.g., a racemic solution using conventional techniques, such as for example, gas chromatography. Moreover, the present application includes every possible combination of each R group, whether explicitly identified or not.

It is contemplated that all embodiments of the invention can be combined with one or more other embodiments, even those described under different aspects of the invention.

As used herein, the term "acyl" has its art-recognized meaning and refers to a group represented by the general formula hydrocarbylC(O)—, preferably alkylC(O)—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, such as from 1 to 8. Likewise, preferred cycloalkyls have from 3-10 carbon atoms in their ring structure, and more preferably have 5, 6 or 7 carbons in the ring structure.

Moreover, unless otherwise indicated, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "alkylamino", as used herein, refers to an amino group substituted with at least one alkyl group.

The term "amide", as used herein, refers to a group

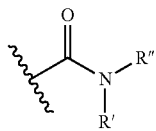

wherein R' and R" each independently represent a hydrogen or hydrocarbyl group, or R' and R" taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

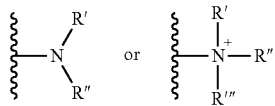

wherein R', R", and R''' each independently represent a hydrogen or a hydrocarbyl group, or R' and R" taken together with the N atom to which they are attached complete a heterocycle having from 4 to 8 atoms in the ring structure.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" are used interchangeably herein and mean halogen and include chloro, fluoro, bromo, and iodo.

The terms "heteroaryl" and "hetaryl" include substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The terms "heterocyclyl", "heterocycle", and "heterocyclic" refer to substituted or unsubstituted non-aromatic ring structures, preferably 3- to 10-membered rings, more preferably 3- to 8-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioether", as used herein, is equivalent to an ether, wherein the oxygen is replaced with a sulfur.

According to an embodiment of the invention, methods are provided for treating or ameliorating the effects of diabetes. Such methods comprise administering to a patient an effective amount of a compound of the present invention, which may, although not wishing to be bound by a particular theory, be a vesicular monoamine transporter type 2 (VMAT2) antagonist, even if a weak VMAT2 antagonist. In certain embodiments, such methods may comprise intravenously administering to a patient in need of such treatment, e.g., a diabetic patient, about 1.6 mg/kg body weight of a compound of the present invention. In other embodiments, such methods may comprise intravenously administering to a patient in need thereof about 2 mg/kg body weight of a compound of the present invention.

According to another embodiment of the invention, methods are provided for treating or preventing hyperglycemia, which comprises administering to a patient an effective amount of a compound of the present invention. In certain embodiments, such methods may comprise intravenously administering to a patient in need thereof, e.g., a hyperglycemic patient, about 1.6 mg/kg body weight of a compound of the present invention. In other embodiments, such methods may comprise intravenously administering to a patient in need thereof about 2 mg/kg body weight of a compound of the present invention.

As used herein in relation to insulin production, glucose homeostasis, and glucose levels, "normalize," "normalizing," "regulate," "regulating," or like terms mean to exert control of those processes through administration of a compound of the present invention to a patient whose insulin production and/or glucose levels deviate from a normal clinical value. Also, a "subject" is a mammal whose insulin production and/or glucose levels deviate from a normal chemical value.

In the Examples, representative methods for determining monoamine levels, islet β-cell insulin secretion levels, insulin and glucagon levels, and insulin production and blood/serum glucose levels in, e.g., a human patient are described. The present invention, however, embraces any art-recognized method for making such determinations. For example, a patient's blood glucose (BG) levels may be monitored and/or determined using an Accu-Check blood glucose monitoring system (Roche Diagnostics, Sommerville, N.J.).

In the present invention, an "effective amount" or "therapeutically effective amount" of a compound of the present invention is an amount of such a compound that is sufficient to effect beneficial or desired results as described herein. In terms of treatment of a mammal, e.g., a human patient, an "effective amount of a compound of the present invention" is an amount sufficient to treat, manage, palliate, ameliorate, or stabilize a condition, such as diabetes (including type-1 or type-2) or hyperglycemia, in the mammal.

Typically, in the present invention, an effective amount of a compound of the present invention is between about 0.2 mg/kg body weight to about 5.0 mg/kg body weight of the compound of the present invention or, preferably, 0.5 to about 3.3 mg/kg body weight, such as 1.6 mg/kg body weight or 2 mg/kg body weight. In the present invention, the foregoing amounts may be provided to a patient for the desired treatment course. Preferably, during a course of treatment, no more than about 3.3 mg of a compound of the present invention is administered.

In the present invention, when a range is stated for a particular parameter, e.g., an effective amount, all values within that range, including the endpoints, are intended to be included. In addition to the foregoing, effective dosage forms, modes of administration, and dosage amounts of the compound of the present invention may be determined empirically, and making such determinations is within the skill of the art in view of the disclosure herein. It is understood by those skilled in the art that the dosage amount will vary with the route of administration, the rate of excretion, the duration of the treatment, the identity of any other drugs being administered, the age, size, and species of mammal, and like factors well known in the arts of medicine and veterinary medicine. In general, a suitable dose of a compound of the present invention according to the invention will be that amount of the compound of the present invention, which is the lowest dose effective to produce the desired effect. The effective dose of a compound of the present invention maybe administered as one, two, three, four, five, six or more sub-doses, administered separately at appropriate intervals throughout the day.

A compound of the present invention may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. In the present invention, a preferred route of administration is intravenous. Further, a compound of the present invention may be administered in conjunction with other treatments. A compound of the present invention or composition containing such a compound may be encapsulated or otherwise protected against gastric or other secretions, if desired.

While it is possible for a compound of the present invention to be administered alone, it is preferable to administer the compound of the present invention as a pharmaceutical formulation (composition). Pharmaceutically acceptable compositions of the invention comprise one or more compound of the present invention as an active ingredient in admixture with one or more pharmaceutically-acceptable carriers and, optionally, one or more other compounds, drugs, ingredients and/or materials. Regardless of the route of administration selected, the compounds of the present invention are formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound of the present invention. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound of the present invention may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more compound of the present invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, and/or solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods and compositions of the present invention. These examples are illustrative only and are not intended to limit the scope of the invention in any way.

EXAMPLES

Example 1

Materials and Methods

Drugs and Reagents.

L-epinephrine bitartrate, STZ, D-glucose, and sodium citrate were obtained from Sigma Chemical Company (St. Louis, Mo.). All cell culture media and supplements were obtained from Invitrogen (Carlsbad, Calif.). Tissue culture plates were obtained from Falconware (Becton-Dickinson, Inc., Oxnard, Calif.). Tetrabenazine and dihydrotetrabenazine were obtained from the National Institute of Mental Health's Chemical Synthesis and Drug Supply Program.

Experimental Animals.

All animal studies were reviewed and approved by the Institutional Animal Care and Use Committee (IACUC) at Columbia University's Medical School. All experiments were performed in accordance with the IACUC approved procedures. Normal male Lewis rats (100-400 grams) were obtained from Taconic (Taconic Inc., Germantown, N.Y.) and were housed under conditions of controlled humidity (55±5%), temperature (23±1° C.), and lighting (light on: 06.00-18.00 hours) with free access to standard laboratory rat chow and water. Rats were handled daily to minimize non-specific stress for more than 7 days before the experiments began. In most experiments, it was necessary to measure blood glucose in fasting animals. For these groups, food was removed at the beginning of the light cycle, 6 hours before glucose levels were measured. Diabetes mellitus was induced by intraperitoneal injection of streptozotocin (Sigma Chemical Co., St. Louis, Mo.) (25 to 50 mg/kg) to animals (100 to 150 grams) that had been fasted 4 hours to enhance the effectiveness of STZ treatment.

The STZ solution was prepared fresh by dissolving it in 0.1 M citrate buffer (pH 5.5) and terminally sterile filtered. Control Lewis age and weight matched rats received a 0.5 ml/kg citrate vehicle alone via intraperitoneal injection. Sixty minutes prior to intraperitoneal glucose tolerance testing (IP-GTT), anesthesia of male Lewis rats was induced with isoflurane (3-4% in oxygen) and maintained with 1-2% isoflurane in oxygen. Anaesthetized rats were administered TBZ and other indicated compounds at the indicated dose by intravenous (i.v.) injection using the penile vein. TBZ was dissolved in neat sterile dimethylsulfoxide (DMSO) and diluted (always more than 10 fold) in sterile saline. Rats received injections of vehicle alone (10% DMSO in saline) or reserpine (in saline). Animals recovered fully before receiving IPGTT.

Blood Glucose, Insulin, Glucagon and Intraperitoneal Glucose Tolerance Tests Measurements.

Blood samples were collected from a superficial blood vessel in the tails of the rats following 6 hours of fasting between 12:00 noon and 2:00 p.m. The fasting blood glucose (BG) levels of the rats were measured using an Accu-Check blood glucose monitoring system (Roche Diagnostics, Sommerville, N.J.). Intraperitoneal glucose tolerance tests (IP-GTT) were performed in 6 hour fasting un-anaesthetized animals. Briefly, after baseline BG measurements, animals received an intraperitoneal (i.p.) injection of 1 gram glucose/kilogram body weight. To minimize stress during the procedure, rats were handled by the same operator during acclimatization and later during weighing and IPGTT. Blood samples (approximately 30 µl) were collected at baseline and then again 15, 30, 60, 90, and 120 minutes following i.p. glucose administration. BG concentrations were measured immediately on these samples and the remainder processed.

Plasma was immediately separated by centrifugation at 3000×g for 15 minutes and then stored at −20° C. until analysis. Insulin and glucagon concentration measurements in rat plasma were performed by ELISA as per the manufacturer's instructions using kits from Linco Research Inc. (St. Charles, Mo.) and Alpco Diagnostics (Salem, N.H.), respectively. To validate the test, saline injections were performed by the same method. During this experiment, glucose concentration did not differ from baseline at each time point (data not shown). The area under the IPGTT glucose concentration×time curve (AUCIPGTT) was calculated by the trapezoidal rule. The area under the insulin or glucagon concentration×time curve (AUC INS or AUC GCG) was calculated in a similar manner. For Lewis rats receiving STZ, the animals were considered diabetic when they showed abnormal IPGTT responses and fasting BG values above about 300 mg/dL on two or more occasions.

Human Islet Tissue and Glucose-Stimulated Insulin Secretion.

The islet tissue used in these studies was obtained with institutional review board approval. Pancreas digestion and islet isolation were performed using minor modifications of the Edmonton purification protocol. (Shapiro, A. M., J. Lakey et al. "Islet preparation in seven patients with type I diabetes mellitus using a glucocortoid-free immunosuppressive regimen." *New England Journal of Medicine* 343(4):230-8, (2000)) The determination of islet cell mass, viability, and purity were also performed. Purified islets were cultured in CMRL 1066 culture media with 10% fetal bovine serum at 37° C. in humidified air (5% $CO_2$) for 18 to 24 hours. The human islet insulin secretory response was performed according to a procedure described by the Edmonton group. (Id.) Briefly, after an overnight culture, islets were incubated with either low or high concentrations of glucose for 2 hours at 37° C. and 5% $CO_2$. The supernatant was collected for insulin measurement. Insulin concentrations in these experiments were analyzed with a human insulin enzyme-linked immunosorbent assay (ELISA) kit (ALPCO Insulin ELISA kit, Windham, N.H.). In some experiments TBZ, DTBZ or epinephrine was added to the cultures before glucose stimulation.

Dopamine Measurements.

Anaesthetized rats received an intravenous injection of TBZ and were sacrificed one hour later. Euthanasia was performed by exsanguination of the anesthetized animal. Brain and pancreas were harvested as quickly as possible and frozen at −80° C. until use. Frozen tissue was pulverized in a liquid nitrogen cooled mortar and extracted in 0.01 N HCl. The tissue extract was centrifuged at 10,000×g at 4° C. to remove debris and the total protein was estimated by reading the absorbance at 280 nm. The concentration of dopamine in the extract was estimated using an ELISA kit from Rocky Mountain Diagnostics (Colorado Springs, Colo.) per the manufacturer's instructions and normalized to the extract protein concentration.

Quantitation of VMAT2 and Proinsulin Transcript Abundance in Pancreata of Lewis Rats.

Harvesting of pancreata was performed by opening the anesthetized rats with a midline incision and reflecting the liver, stomach and small intestines to expose the pancreas. The cavity was then bathed with 5 ml of RNAlater (Ambion, Austin, Tex.) per the manufacturer's recommendations. The head, body and tail of the pancreas were dissected under RNAlater and removed to a 25 mm plastic Petri dish containing sufficient RNAlater to cover the excised tissue. The pancreas was cut into approximately 2×2×2 mm sections and transferred to fresh RNAlater and stored overnight at 4° C. Total pancreatic RNA was isolated and specific transcript abundances were measured by real-time quantitative RT-PCR. The conditions used were as follows: one cycle at 95° C. for 900 seconds followed by 45 cycles of amplification (94° C. for 15 seconds, 55° C. for 20 seconds, and 72° C. for 20 seconds). The oligonucleotides were synthesized by Invitrogen. The primer sequences used were as follows:

```
                                      (SEQ ID NO: 1)
5'-CTTCGACATCACGGCTGATGG-3' (Cyclophilin A-5')
and
                                      (SEQ ID NO: 2)
5'-CAGGACCTGTATGCTTCAGG-3' (Cyclophilin A-3'), (SEQ ID NO: 3)
5'-GCC CTG CCC ATC TGG ATG AT-3' (VMAT2-5')
and
                                      (SEQ ID NO: 4)
5'-CTT TGC AAT AGC ACC ACC AGC AG-3' (VMAT2-3'), (SEQ ID NO: 5)
5'-CCC AGG CTT TTG TCA AAC-3' (rINS1/2-5')
and
                                      (SEQ ID NO: 6)
5'-CTT GCG GGT CCT CCA CTT 3' (rINS1/2-3').
```

The relative amounts of mRNA were calculated by the comparative cycle threshold (CT) method. Such values were then normalized by cyclophilin A expression.

Quantitation of VMAT2 and Insulin Protein in Pancreas Lysates by Western Blot.

Western blot analysis was conducted of brain and pancreas tissue obtained from control and diabetic streptozotocin treated rats. Briefly, sample tissue were prepared in RIPA buffer (1×PBS; 1% Igepal CA-630; 0.5% sodium deoxycholate; 0.1% SDS; 10 mg/ml complete protease inhibitor cocktail (Roche Inc, Palo Alto, Calif.)) at 4° C. Protein concentrations were determined using a Bio-Rad protein assay (Bio-Rad Inc., Hercules, Calif.). Protein separation and gel transfer were carried out using the NuPage/Novex XCELLII system for 4-12% gradient Bis-Tris gels and MOPS running buffer (Invitrogen, Carlsbad, Calif.). After transfer, PVDF membranes were washed in Tris-Buffered Saline (TBS), blocked in TBS-5% non-fat milk and incubated with a rabbit anti-hVMAT2-Ct primary antibody (Chemicon, Temecula, Calif.) or anti-insulin primary antibody (Phoenix Pharmaceuticals, Burlingame, Calif.) at 1:1000 in TBS-T (TBS, 0.075% Tween-20) overnight at 4° C. The membranes were washed in TBS-T and incubated with a goat anti-rabbit secondary antibody conjugated with horseradish peroxidase (HRP) (Santa Cruz Biotechnology, Santa Cruz, Calif.) at 1:3333 in TBS-T for 1 hour at room temperature and washed again in TBS-T. The membranes were placed in West Pico chemiluminescent solution (Pierce, Rockford, Ill.) and developed on a FujiFilm developer.

Immunohistochemistry.

Cadaveric pancreas tissue was fixed and paraffin embedded by standard methods. Sections were deparaffinized with a series of graded alcohols and xylenes. Antigen retrieval was achieved by microwave treatment with 10 mM sodium citrate (pH 6) for 10 minutes. Endogenous peroxidase was quenched with a 3% hydrogen peroxide solution for 20 minutes. Sections were then blocked with CAS Block (Zymed, San Francisco, Calif.) followed by incubations with (1) anti-VMAT2 primary antibody overnight at 4° C. (1:200, Chemicon); (2) biotinylated goat anti-rabbit IgG secondary antibody (1:200, Vector, Burlingame, Calif.) for 1 hour at room temperature; and (3) HRP-Streptavidin (Zymed) for 1 hour at room temperature. Color was then developed with an enhanced DAB kit (Abcam, Cambridge, Mass.) and sections were lightly counterstained with hematoxylin (Vector).

Statistical Analysis.

All results are presented as means±SEM or as indicated in the text. Statistical strength of associations was estimated by the method of Student t-testing.

Example 2

Materials and Methods

Drugs and Reagents.

Tetrabenazine, tetrahydroberberine (THB), butamol, reserpine, emetine and olanzapine are commercially available or are obtained from the National Institute of Mental Health's Chemical Synthesis and Drug Supply Program. The synthetic protocols for HG-1, HG-2, HG-3, HG-4, HG-6, and HG-11 are described within Example 4 below. The synthesis of other HG-designated compounds tested will be apparent to one of ordinary skill in the art in view of the synthetic Schemes described below as well as the synthetic protocols in Example 4 for particular compounds.

The structures of THB, butamol, reserpine, emetine, and HG-6 are shown below:

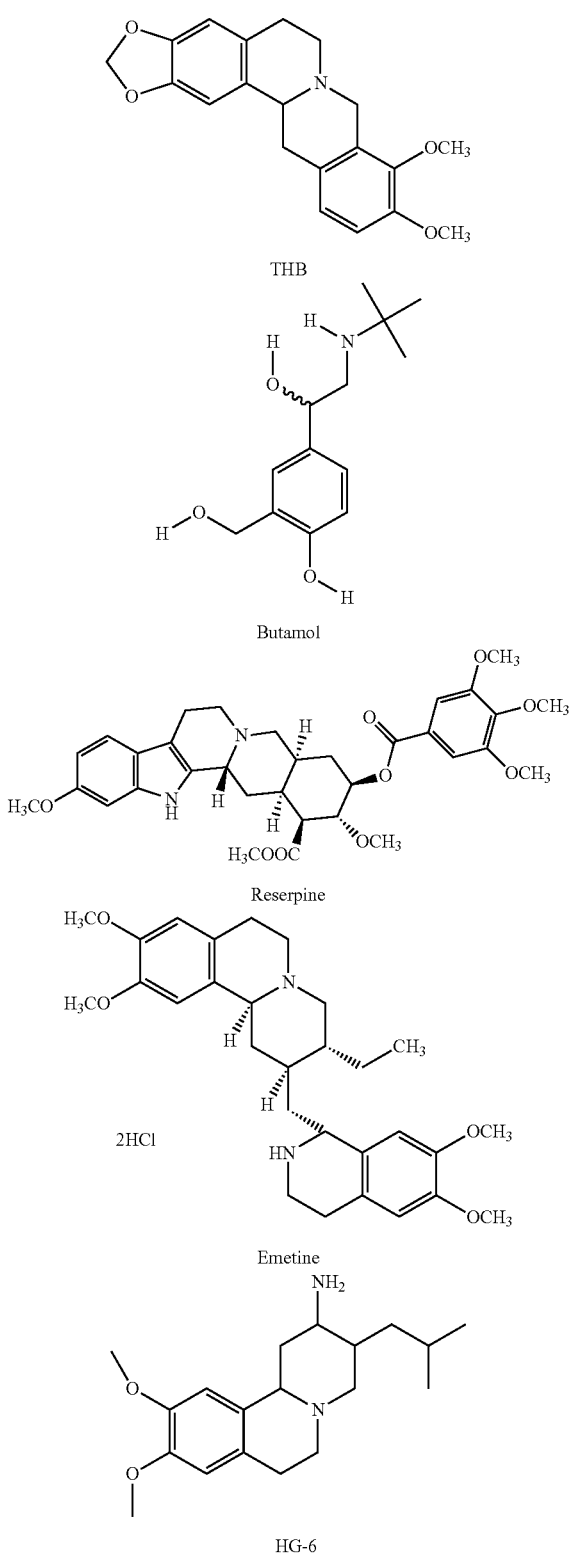

Experimental Animals.

All animal studies were conducted as described in Example 1.

Anaesthetized rats were administered TBZ, THB, butamol, reserpine, emetine, or HG-6 at a dose of approximately 2-3 mg/kg body weight by intravenous (i.v.) injection using the penile vein. TBZ, THB, butamol, reserpine, emetine, and HG-6 were each separately dissolved in neat sterile dimethylsulfoxide (DMSO) and diluted (always more than 10 fold) in sterile saline. Rats received injections of vehicle alone (10% DMSO in saline) or reserpine (in saline). Animals recovered fully before receiving IPGTT.

Blood Glucose, Insulin, Glucagon and Intraperitoneal Glucose Tolerance Tests Measurements.

Blood samples were collected from a superficial blood vessel in the tails of the rats following 6 hours of fasting between 12:00 noon and 2:00 p.m. The fasting blood glucose (BG) levels of the rats were measured using an Accu-Check blood glucose monitoring system (Roche Diagnostics, Sommerville, N.J.). Intraperitoneal glucose tolerance tests (IP-GTT) were performed in 6 hour fasting un-anaesthetized animals. Briefly, after baseline BG measurements, animals received an intraperitoneal (i.p.) injection of 1 gram glucose/kilogram body weight. To minimize stress during the procedure, rats were handled by the same operator during acclimatization and later during weighing and IPGTT. Blood samples (approximately 30 μl) were collected at baseline and then again 15, 30, 45, 60, 90, and 120 minutes following i.p. glucose. BG concentrations were measured immediately on these samples and the remainder processed.

PET Study Protocol.

To test binding to VMAT2 in beta cells, PET scans were performed on 12-14 week old Lewis Male rats. Prior to imaging, the animals were anesthetized by isoflurane inhalation. After a transmission scan of the area of interest had been acquired (used to perform attenuation correction of the emission data), the radioligand [11C]DTBZ was administered (0.5-1.0 μCi/gm) in saline as bolus injection via the penile vein. PET scans of the animals were acquired dynamically to 90 min post injection on a Concorde microPET-R4 (CTI Molecular Imaging, Knoxville, Tenn., USA). The scanner provided a 100×80 mm field of view with a reconstructed resolution of 2.25 mm in the central 40 mm of the field of view. At thirty minutes post injection of [11C]DTBZ, the animals received a second injection via the penile vein of cold analog. PET data were processed using attenuation correction matrix obtained by transmission scans and images were reconstructed using Fourier rebinning, followed by two-dimensional, filtered back projection using microPET manager software (CTI Molecular Imaging).

The Effect of HG-3 on Dipeptidyl Peptidase IV (DDP-IV).

The effect of HG-3 on DDP-IV was determined by assays provided by BPS Bioscience, Inc. (San Diego, Calif.).

Example 3

Results & Analysis

Glucose Tolerance in Lewis Rats is Improved by TBZ.

Older Lewis rats have a relative glucose intolerance compared to younger animals during an IPGTT. To explore the role of VMAT2 in insulin secretion and to better demonstrate the possible value of VMAT2 as a potential therapeutic target in diabetes, older male Lewis rats were selected for IPGTT testing with and without a single dose of tetrabenazine. A dose of tetrabenazine approximately three to ten fold higher than the equivalent human doses currently used to treat movement disorders was used in this example. Following TBZ administration, but before glucose challenge, no reproducible differences were observed in the baseline fasting glucose concentration of control animals (data not shown).

Figure 2:
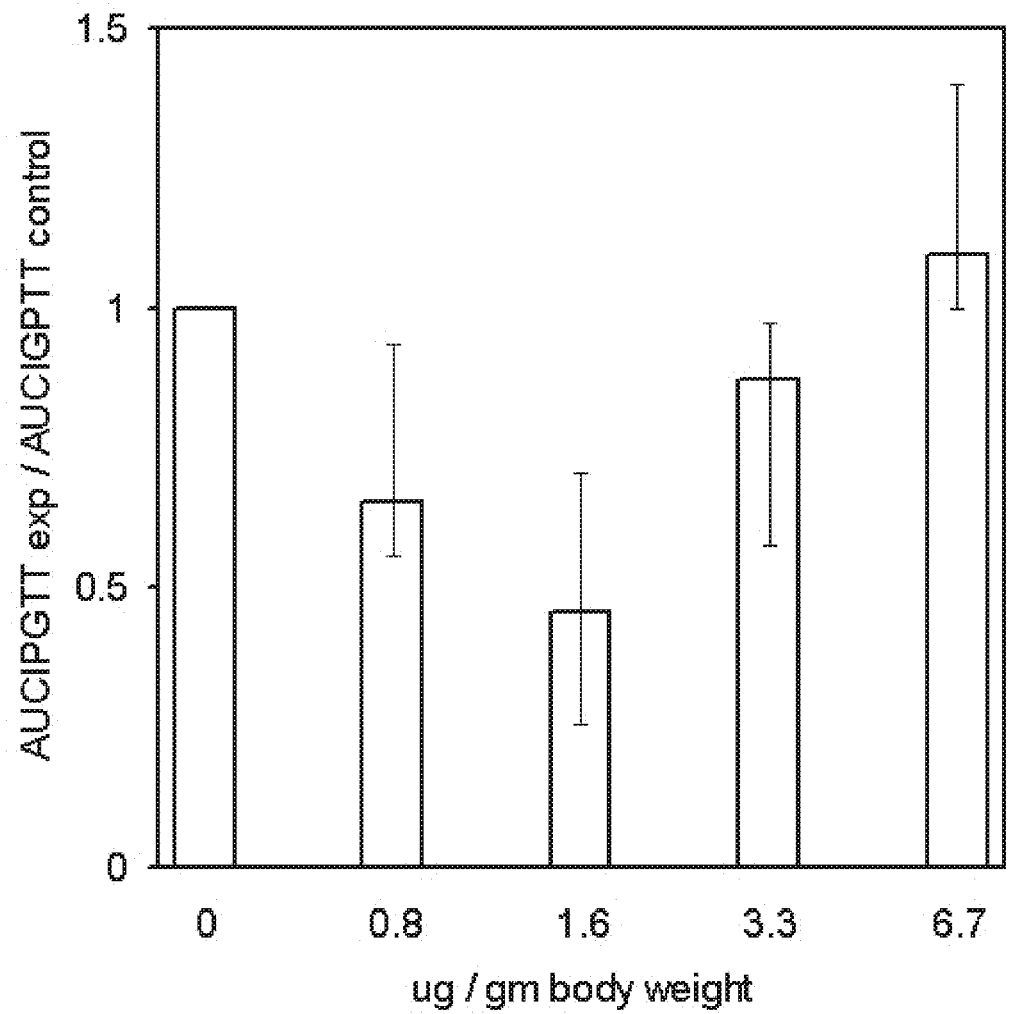
FIG. 2. TBZ reduces the blood glucose excursion in a dose dependent manner. Area under the curve from glucose tolerance tests (AUCIPGTT) of Lewis rats treated with varying doses of tetrabenazine. A baseline untreated IPGTT was determined for each animal. One week later, a second IPGTT was performed with varying doses of TBZ. Two or more animals were used at each dose level. The area under the curve was calculated for each test and the results for TBZ-treated animals were normalized to their respective baseline measurement. Results are presented as the mean of two or more measurements and the error bars indicate the highest and lowest measurement at the indicated dose.

Following tetrabenazine treatment and glucose challenge, however, a significant change in the size and shape of the glucose disposition curve was observed during IPGTT (FIG. 1). For example, the characteristic rise in glucose concentration around 15 minutes after injection was blunted following TBZ administration. A comparison of the areas under the curve during IPGTT reveals that TBZ reduced the glucose excursion by 40-50% at 1.6 µg/gbw (gram body weight). When the dose of TBZ given before IPGTT was varied, a complex dose response effect resulted (FIG. 2).

Figure 3:
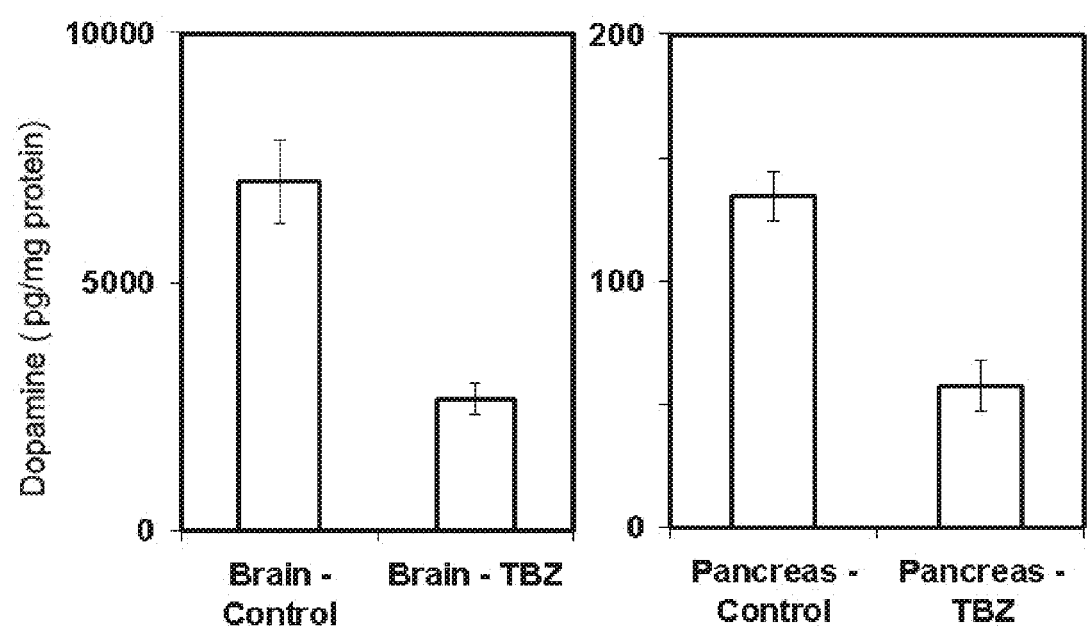
FIG. 3. TBZ reduces the dopamine content of brain and pancreas tissue. TBZ at 1.6 μg/gm body weight was administered intravenously to Lewis rats. One hour later, the animals were euthanized and the brains and pancreata harvested and extracted in buffer. The dopamine concentration in the extract was determined by ELISA and normalized to the total protein content.

Because reserpine also binds to VMAT2, albeit with a higher dissociation constant (but with less selectivity), the effects of a single concentration of reserpine (25 µg/gbm) in the Lewis IPGTT was also tested. It was found that reserpine induced a persistent hyperglycemia and larger AUC IPGTT relative to the untreated controls (data not shown). It is known that tetrabenazine will reduce the concentration of monoamines in the CNS, and that dopamine is a well-known substrate of VMAT2-mediated vesicular transport. Thus, the effects of tetrabenazine on the concentration of the monoamine dopamine in both the pancreas and brain was tested one hour after injection of 10 µg/gm body weight of tetrabenazine. This test demonstrated that TBZ significantly depleted the dopamine content of pancreas and brain (FIG. 3).

Glucose Tolerance in Diabetic Lewis Rats is Improved by TBZ.

Whether the glucose tolerance enhancing effects of TBZ might extend to animals with reduced β-cell mass and impaired glucose tolerance due to STZ-induced diabetes was next examined. For these experiments, younger animals (5-8 weeks of age) were selected—for their better tolerance of induction of diabetes with STZ. From a pool of animals treated with streptozotocin, rats that showed high fasting glucose concentrations and impaired glucose tolerance were selected, which were characterized by high early glucose levels (>300 mg/dl) that peaked and gradually diminished (but did not return to baseline levels within the duration of the two hour IPGTT test).

Figure 4:
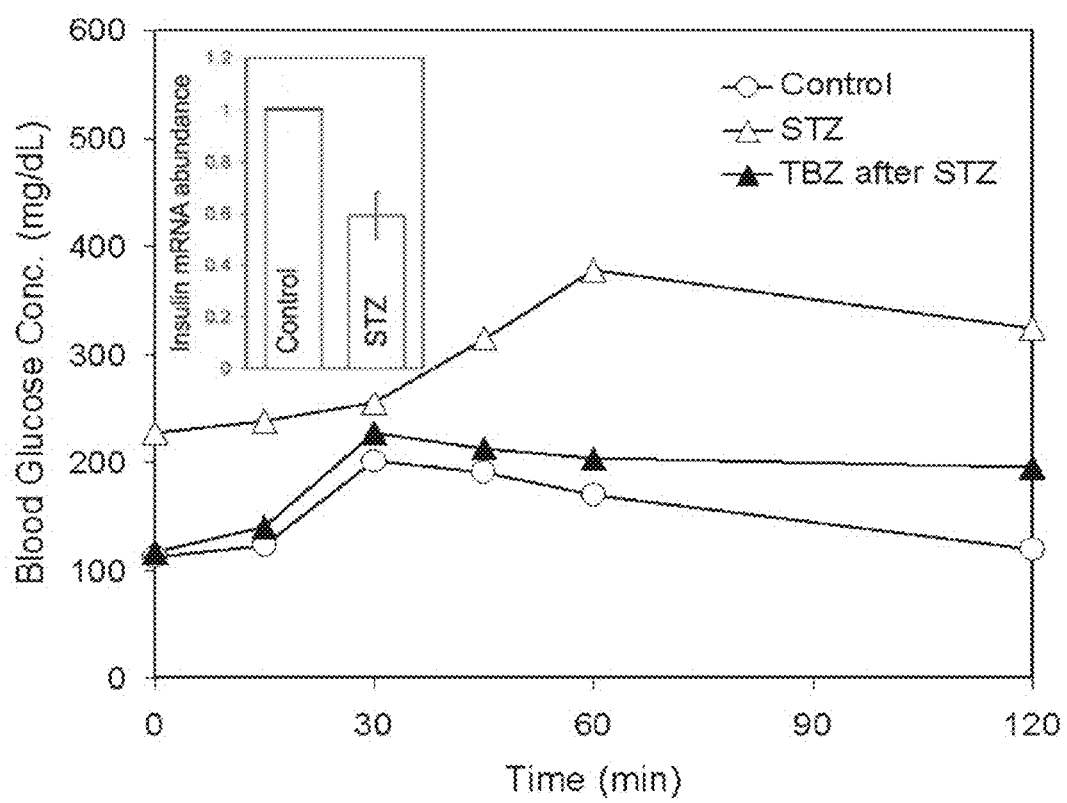
FIG. 4. TBZ reduces the blood glucose excursion during IPGTT in diabetic Lewis rats. Blood glucose values during an IPGTT of Lewis rats (5-7 weeks old) were measured before treatment with streptozotocin (open circle) and following induction of diabetes with streptozotocin (triangles). The IPGTT response was first measured in diabetic rats treated with TBZ (1.6 μg/gm) (closed triangles) and then several days later with vehicle alone (open triangles). Data from a representative experiment in a series of three animals. Inset. The abundance of insulin transcripts in the pancreas of streptozotocin (STZ)-treated animals used in these experiments was measured after IPGTT testing and compared to the mean transcript abundance of a group of three control animals. Error bars represent the standard error of the mean.
Figure 5:
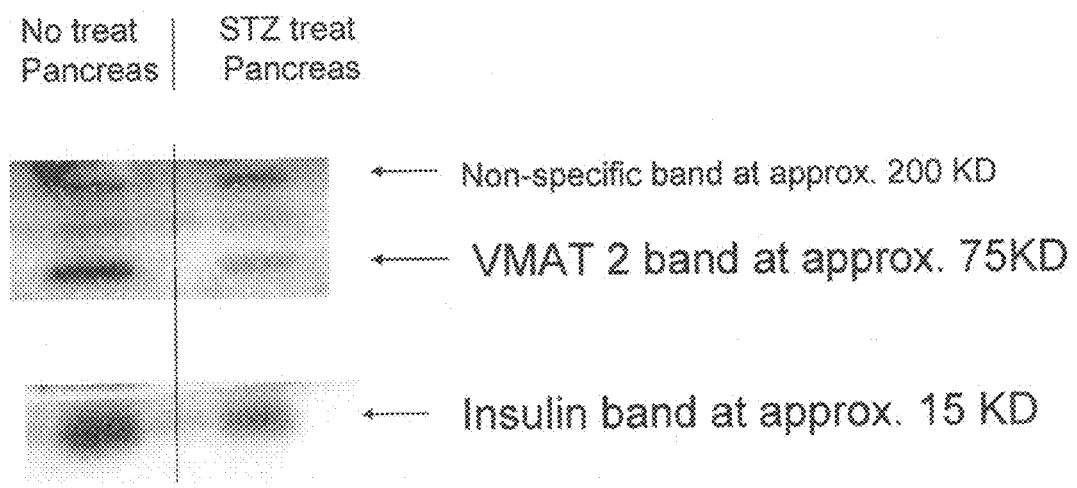
FIG. 5. Quantitation of VMAT2 protein in pancreas of control and STZ-treated Lewis rats. Pancreata were removed en block from control and diabetic Lewis rats and solubilized in SDS page buffer with protease inhibitor cocktail. Lysates were separated in the first dimension by SDS page. Proteins were then transferred electrophoretically to membranes, blocked and probed with either anti-VMAT2 or anti-insulin antibodies. The bands were then developed with a HRP-conjugated secondary antibody and chemiluminescent substrate solution.

During IPGTT testing, blood glucose levels were returned to control or near normal levels at around sixty minutes following i.v. injection of TBZ, but before i.p. glucose challenge (FIG. 4). Following glucose challenge, and similar to normal Lewis rats treated with TBZ, it was found that TBZ administration resulted in a smaller area under the curve in the IPGTT. The glucose tolerance-enhancing effects of TBZ were not observed if the selected TBZ-untreated animals had initial AUC IPGTT>50,000 minutes×mg/dl (data not shown). The loss of insulin within the endocrine pancreas following STZ treatment was validated by quantitative RT-PCR (FIG. 4 inset). The loss of VMAT2 protein within the pancreas following STZ treatment was also validated by western blotting (FIG. 5).

TBZ Enhances In Vivo and In Vitro Glucose Dependent Insulin Secretion.

Figure 6:
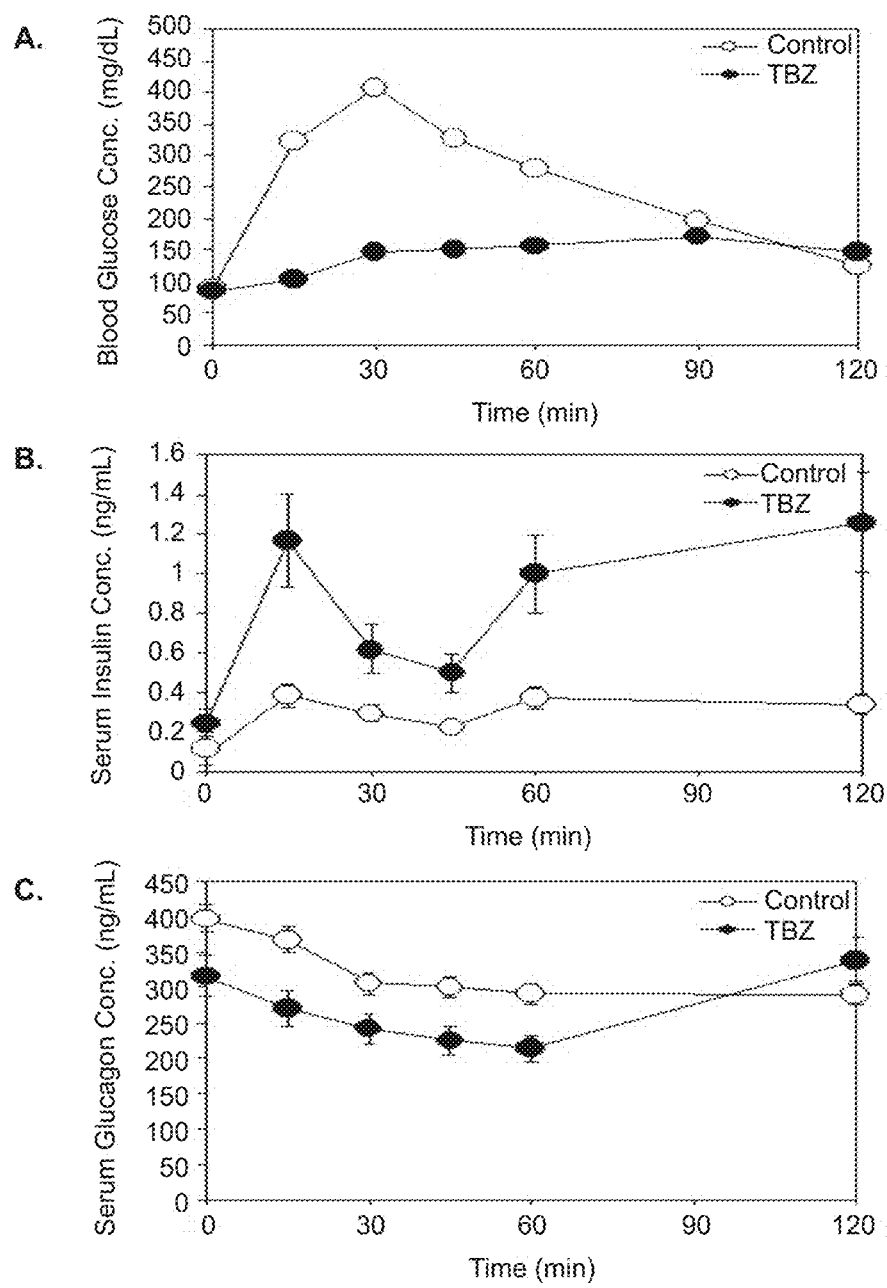
FIG. 6. TBZ alters glucose-stimulated insulin and glucagon secretion in vivo. Serum insulin (B) and glucagon (C) concentrations and blood glucose concentrations (A) were measured during IPGTT of Lewis rats (9-11 week old) treated with vehicle alone (open symbols) or with TBZ (1.6 μg/gm) (closed symbols). Data from a representative experiment in a series of three animals were tested. Measurements are means and standard errors from triplicate determinations of serum/blood samples.

Whether the smaller glucose excursions in IPGTT seen after administration of TBZ were due to increased insulin levels in the plasma after glucose stimulation was next analyzed. Both plasma insulin and glucagon levels from blood samples obtained during IPGTT were measured (FIG. 6). It was found that insulin and glucagon levels were altered by administration of TBZ. Plasma insulin levels were, in general, greater following TBZ and glucose challenge relative to the vehicle treated controls. In four out of five experiments with different animals, the AUC INS with TBZ treatment was greater than two fold the AUC INS of control animals. Plasma glucagon levels were generally lower relative to controls following i.v. TBZ administration and glucose challenge. In three of five experiments, the AUC GCG in the presence of TBZ was 75%-85% less than the AUC GCG measured for the control animals. It was also noted that, prior to glucose challenge, the baseline plasma concentrations of glucagon were sometimes lower than controls, although these differences did not reach statistical significance.

TBZ Enhances Insulin Secretion in Human Cadaveric Islets.

Figure 7:
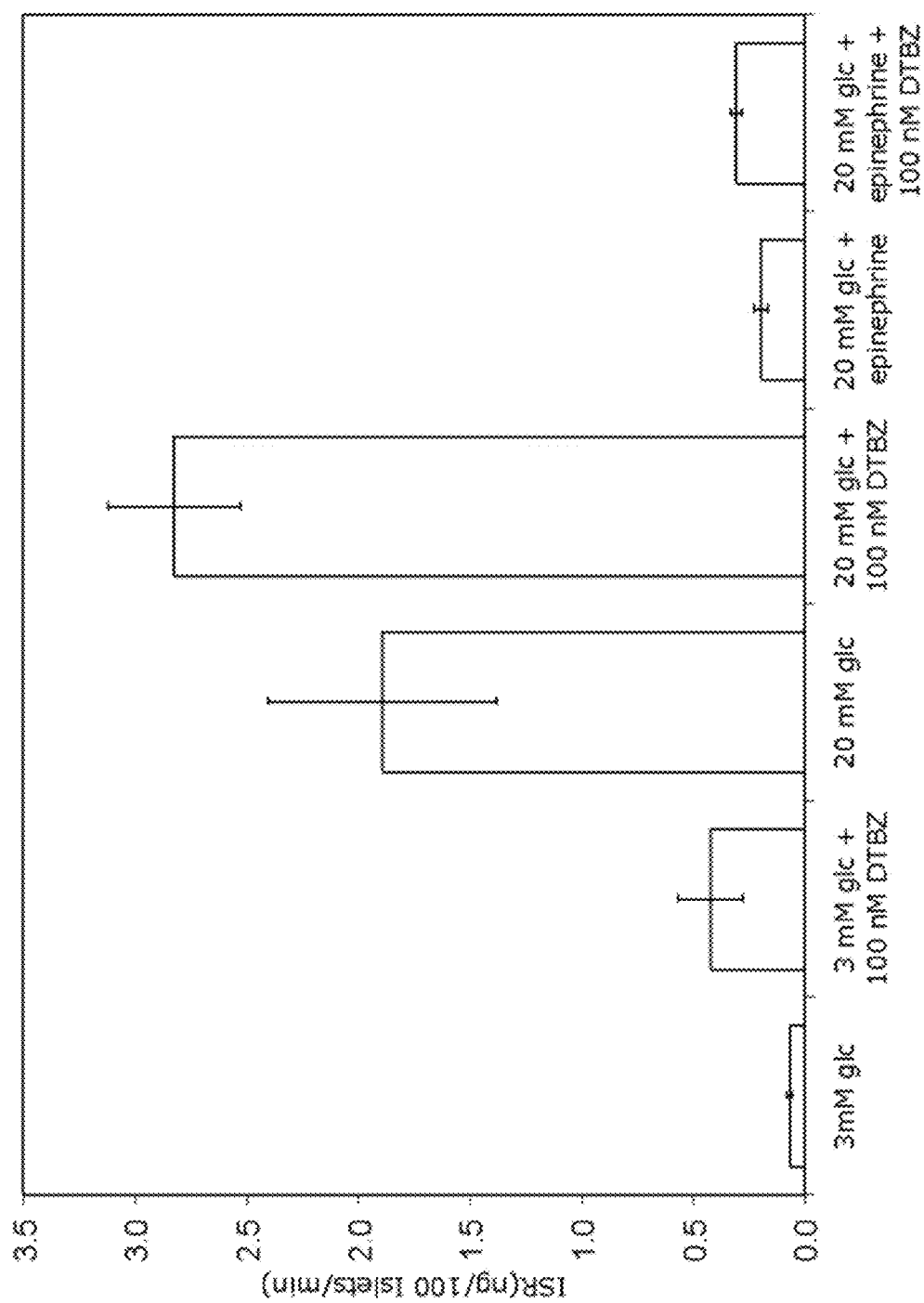
FIG. 7. Dihydrotetrabenazine (DTBZ) enhances glucose-stimulated insulin secretion in human islets ex vivo. Purified cadaveric islets were cultured in high or low glucose-containing media with and without DTBZ and epinephrine. During the incubation period, the insulin secretion rate (ISR) of the islets was determined by ELISA.

Because VMAT2 is located throughout the CNS and glucose homeostasis is regulated by both the autonomic and sympathetic nervous system, whether TBZ was acting centrally and/or locally in islets was next considered. More particularly, because of their availability and clinical relevance, whether TBZ could enhance insulin secretion in purified human islet tissue ex vivo was tested. For these studies, clinical grade human islets that had not been utilized for transplantation were used. The islets were incubated in high and low glucose media with and without dihydrotetrabenazine (DTBZ). It was found that incubation of human islets in DTBZ significantly enhanced the amount of insulin secreted by islets in culture following stimulation by high concentrations of glucose (FIG. 7).

Figure 8:
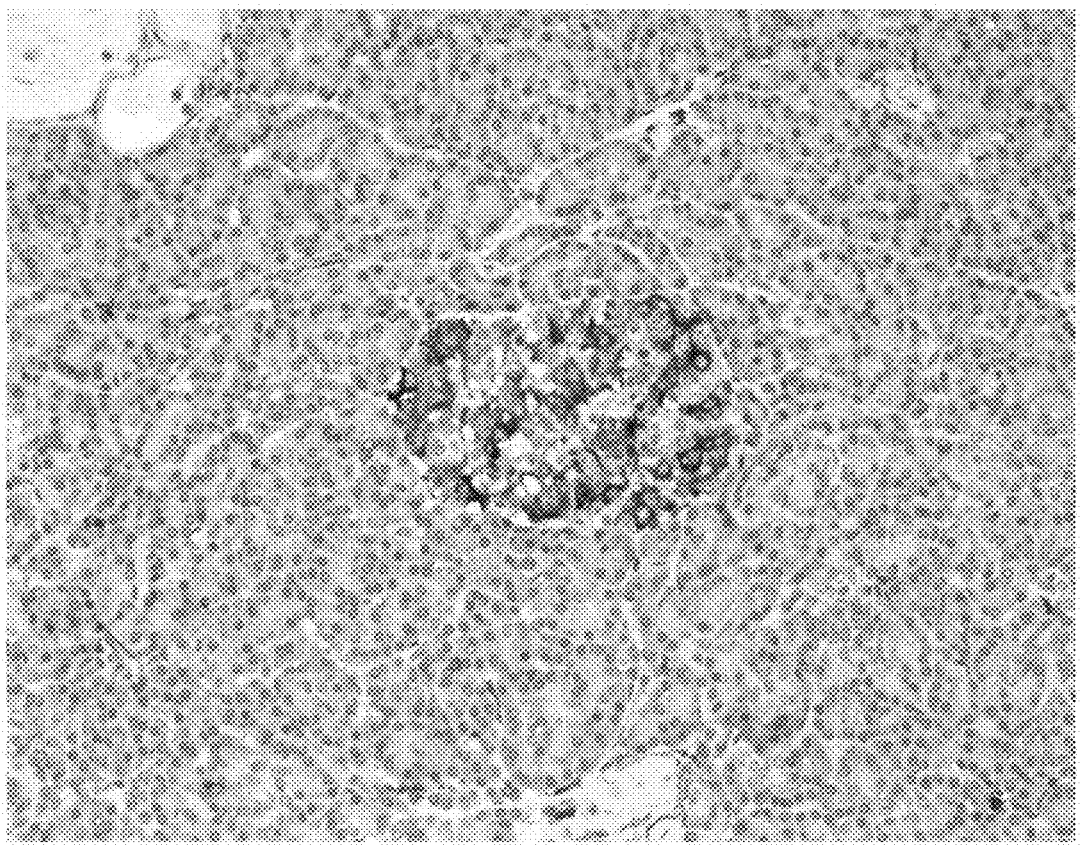
FIG. 8. VMAT2 localizes to human islets in situ. Human cadaveric pancreas tissue was processed for immunohistochemistry and probed with anti-VMAT2 antibodies. The pattern of staining is limited to the central islet of Langerhans and an occasional nerve fiber.

In control experiments, islets were incubated with epinephrine. As expected, epinephrine inhibited secretion of insulin in response to glucose stimulation. In the absence of high glucose stimulation, an increase in insulin secretion mediated by tetrabenazine was not observed (data not shown). Immunohistochemistry of pancreas sections confirmed that VMAT2 is localized to human islets (FIG. 8) and suggests that tetrabenazine mediates its effects on glucose metabolism directly by interfering with VMAT2-mediated monoamine transport within islet tissue.

Glucose Tolerance in Diabetic Lewis Rats is Also Improved by THB, Reserpine, and Emetine.

Figure 10:
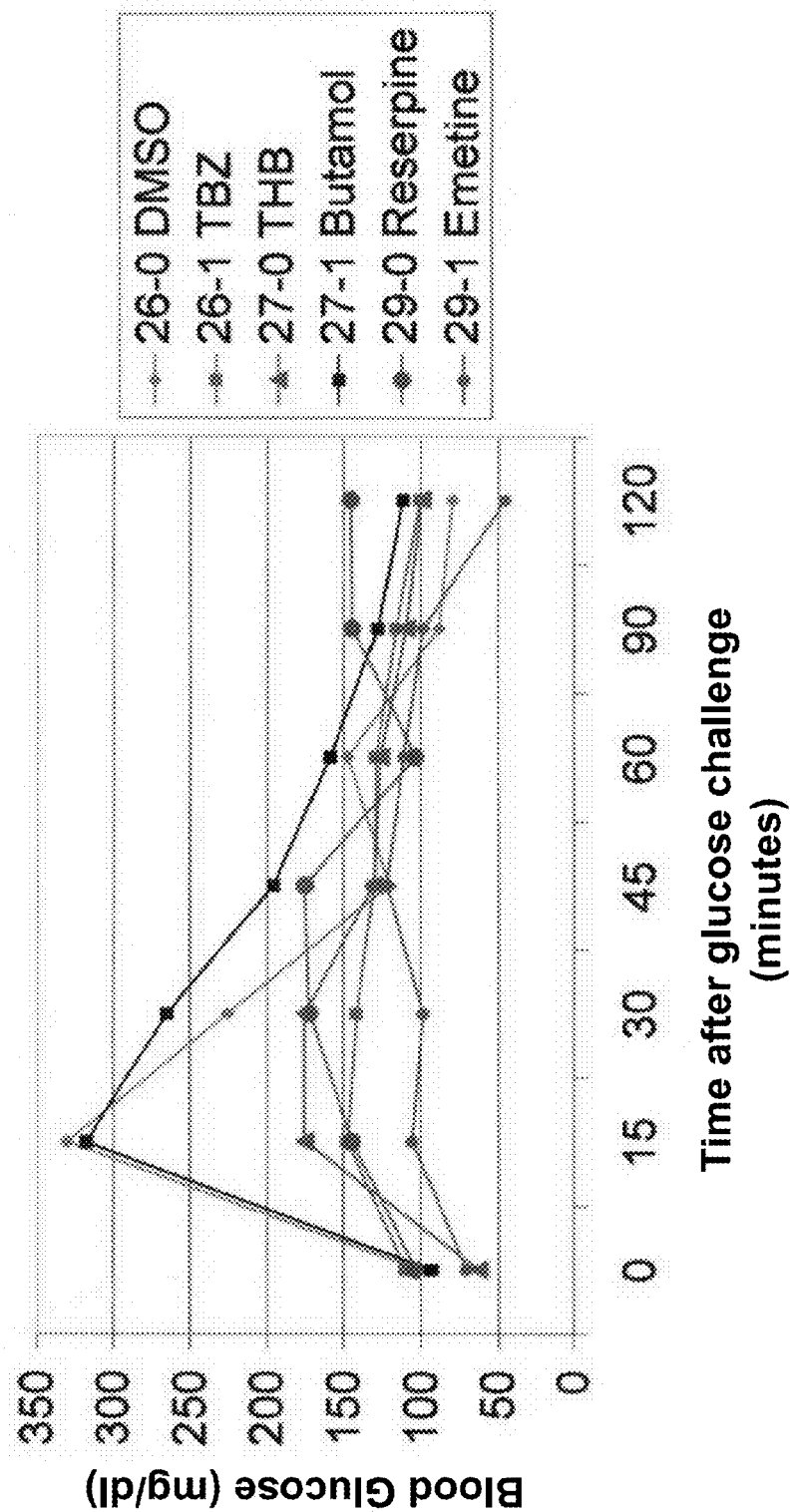
FIG. 10. TBZ, tetrahydroberberine (THB), reserpine, and emetine reduce the blood glucose excursion during an intraperitoneal glucose tolerance test (IPGTT). Butamol does not reduce the blood glucose excursion during an IPGTT. Blood glucose values during an IPGTT of Lewis rats (9-11 weeks old) treated with 2 mg/kg body weight of vehicle (dimethyl sulfoxide (DMSO)) alone (diamonds), TBZ (lighter squares), THB (triangles), butamol (darker squares) reserpine (larger circles), and emetine (smaller circles) are shown.

During IPGTT testing, blood glucose levels were returned to control or near normal levels at around sixty minutes following glucose challenge for those animals treated with an i.v. injection of TBZ, THB, butamol, reserpine, or emetine at dose of 2 mg/kg body weight (FIG. 10). Tetrabenazine, tetrahydroberberine (THB), reserpine, and emetine reduced the blood glucose excursion during an IPGTT. Butamol, however, did not reduce the blood glucose excursion during an IPGTT. Following glucose challenge, it was found that administration of TBZ, THB, butamol, reserpine, or emetine resulted in a smaller area under the curve in the IPGTT.

Glucose Tolerance in Lewis Rats is Also Improved by HG-6.

Figure 12:
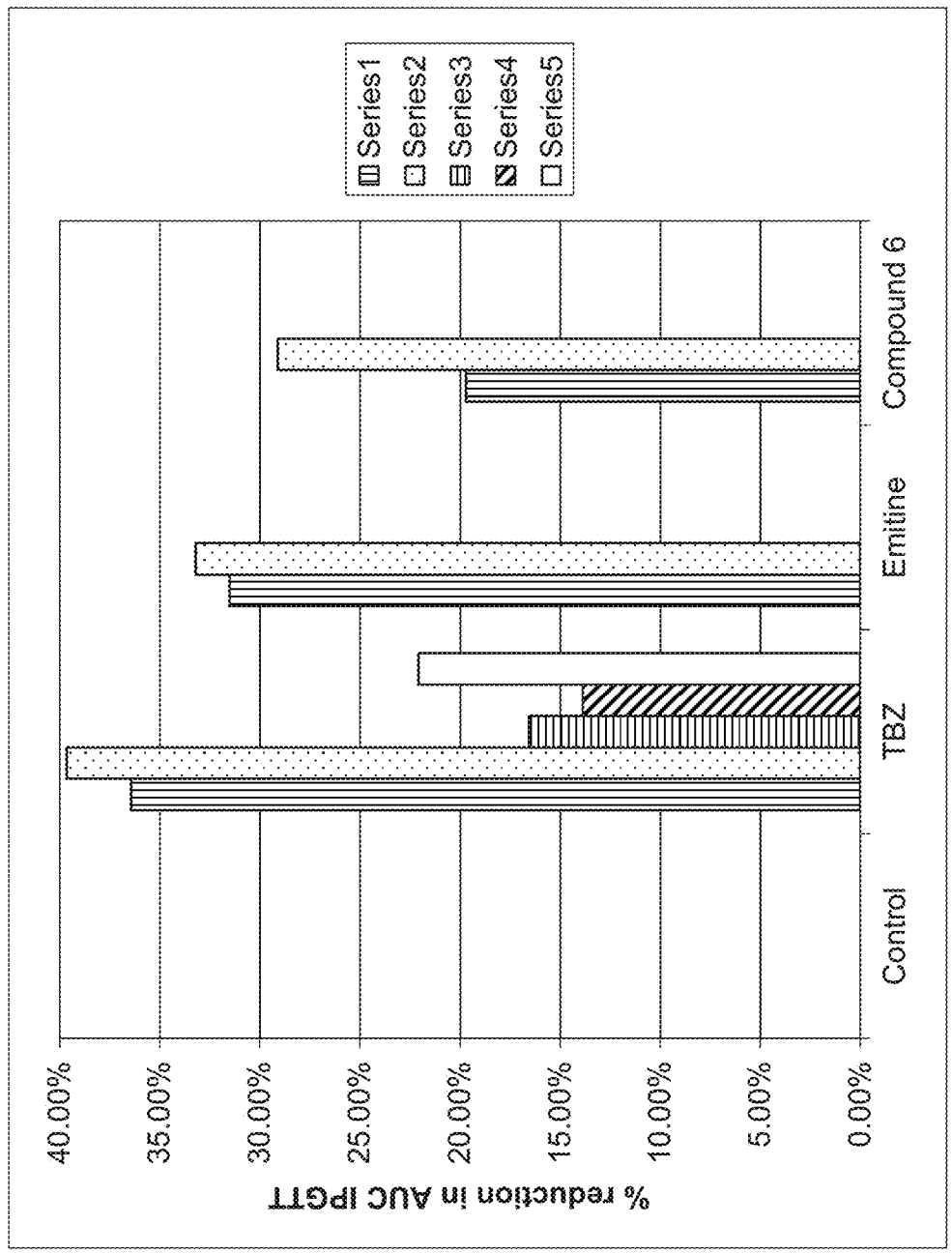
FIG. 12. TBZ, emitine, and HG-6 depress the area under the curve from glucose tolerance tests. Each series is a separate experiment.
Figure 13:
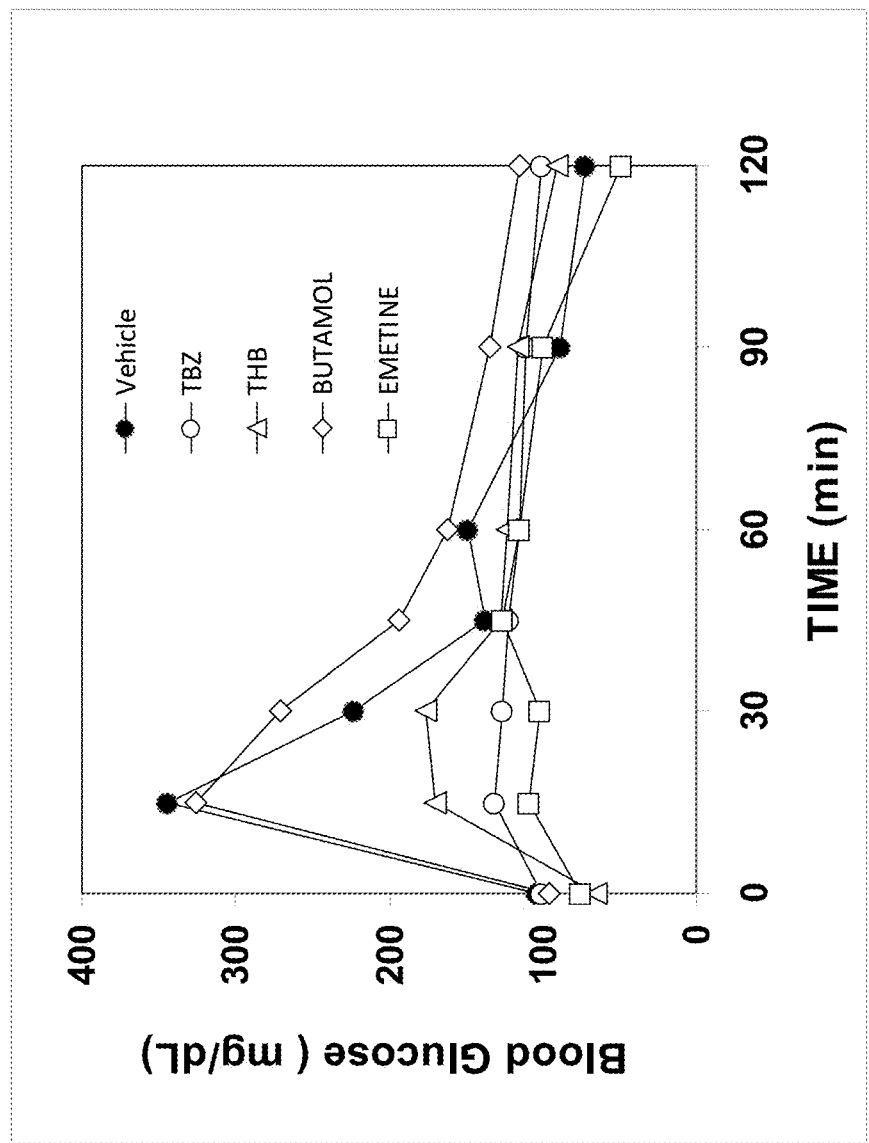
FIG. 13 is a graph of blood glucose concentration vs. time obtained during an intraperitoneal glucose tolerance test (IPGTT) of Lewis rats treated with vehicle alone, or 2 mg/kg body weight of each of TBZ, tetrahydroberberine (THB), butamol and emetine. See also FIG. 10, which additionally shows reserpine. The results show that TBZ, THB and emetine reduced the blood glucose excursion during the IPGTT test.
Figure 14:
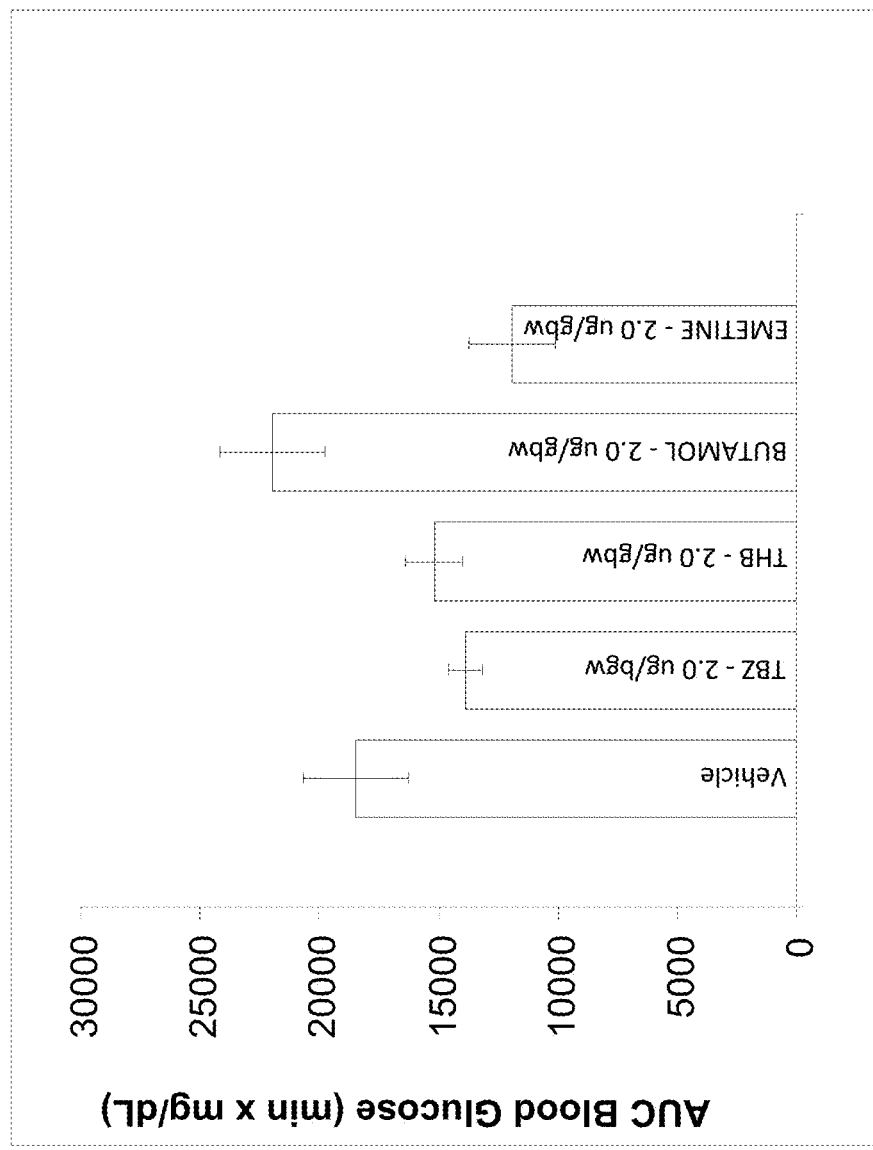
FIG. 14 shows the results of the IPGTT test as in FIG. 13, presented here as AUC Blood Glucose (min×mg/dL) IPGTT. (The dosage is shown as 2.0 μg/gbw (microgram per gram body weight), which is equivalent to 2 mg/kg.) AUC IPGTT for each of TBZ, THB, and emetine treated animals was lower than that for vehicle and butamol treated animals.

Lewis rats were selected for and subjected to IPGTT testing with and without a single dose of TBZ, emetine, and HG-6 (2-3 mg/kg body weight) as previously described. As shown, TBZ, emetine, and HG-6 consistently reduced the blood glucose excursion during an IPGTT, because these compounds consistently suppressed the area under the curve from IPGTT (FIG. 12).

Several previous studies have demonstrated a link between insulin secretion and dopamine. For example, it has been shown that treating Parkinson's patients with a dopamine precursor, L-DOPA, reduces insulin secretion in glucose tolerance tests. In rodent experiments, i.v. administration of L-DOPA has been shown to inhibit glucose-stimulated insulin secretion. Similarly, in culture, analogs of dopamine have been reported to inhibit glucose-stimulated insulin release by purified islets. More recently, it has been demonstrated that mouse n-cells (INS-1E cells), as well as purified rat and human islets, express the dopamine D2 receptor. In these cells and tissues, the D2 receptor was shown to co-localize with insulin in secretory granules. Both dopamine and the D2-like receptor agonist, quinpirole, inhibited glucose-stimulated insulin secretion when tested in primary rat β-cells, and pancreatic islets of rat, mouse, and human origin.

In the above example, it is shown that TBZ depletes the total dopamine content of the pancreas and enhances islet β-cell insulin secretion both in vivo and ex vivo. In light of the foregoing, the following model for the role of VMAT2 in islet function can be constructed. Dopamine, either produced in the exocrine pancreas or locally by β-cells, is transported and stored in insulin containing vesicles. In the presence of tetrabenazine, unsequestered dopamine is destroyed by monoamine oxygenases present in β-cells. Under normal glucose-stimulated insulin secretion, dopamine is also released with insulin and acts either in an autocrine or paracrine fashion to limit glucose-stimulated insulin secretion by other β-cells within the same islet or a distant islet.

Figure 9:
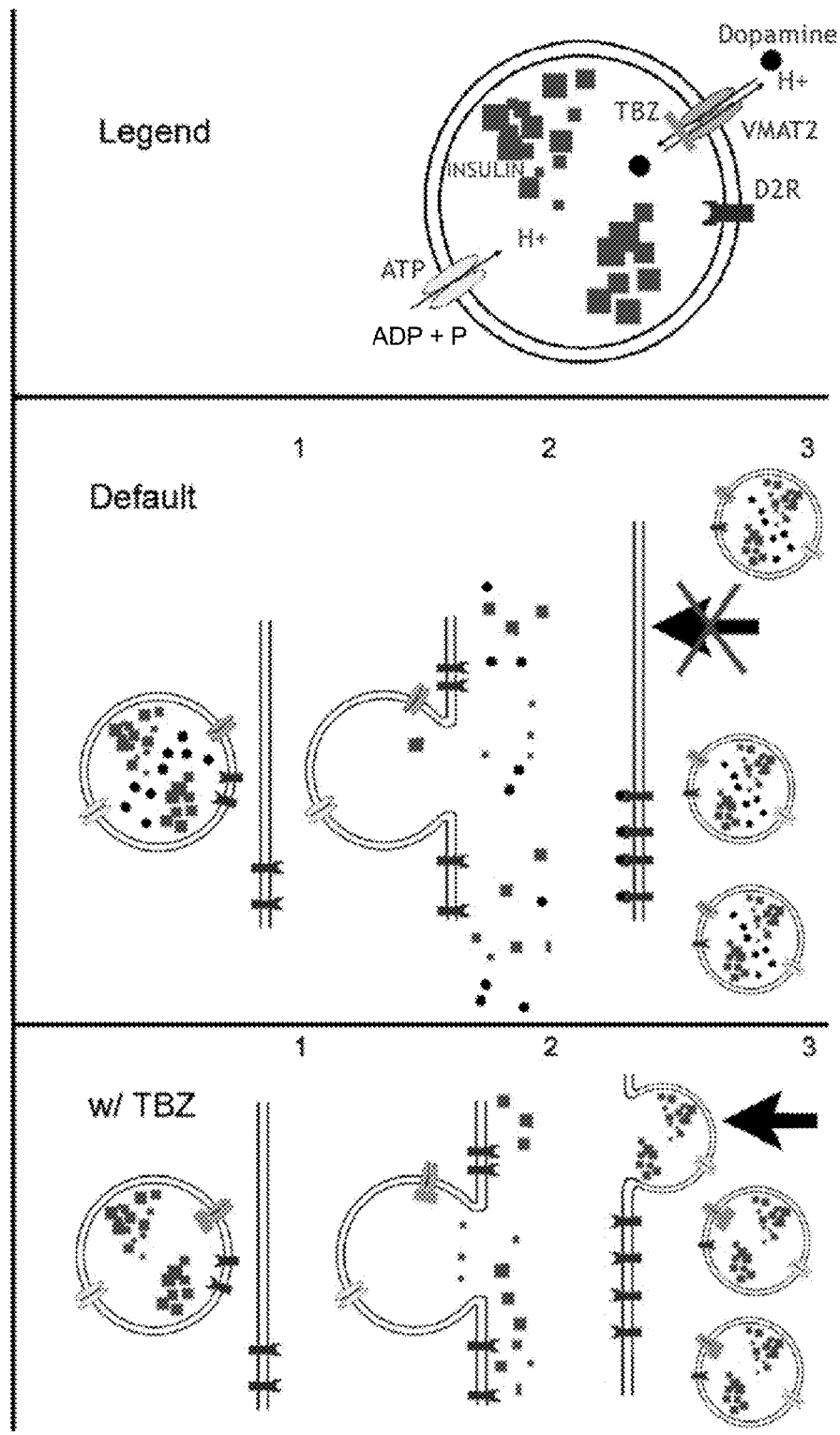
FIG. 9. A diagram showing the effect of TBZ on glucose homeostasis.

In the presence of tetrabenazine, this negative feedback loop is not present and dopamine is not released with insulin and other β-cells are left uninhibited (FIG. 9). This model and the above observations must be interpreted carefully. Tetrabenazine has been used to treat movement disorders for over thirty years and glucose homeostasis related side effects have not been reported. Nevertheless, the above data argue that VMAT2 plays a role in glucose homeostasis and constitutes a target for intervention in (and treatment and/or prevention of) hyperglycemic disorders.

Structure-Activity Relationships (SAR) of Compounds of the Present Invention.

The present invention provides potent hypoglycemic agents, many of which have a dihydropyridone scaffold. HG-1 was identified which is a simplified analog of dihydrotetrabenazine (DTBZ). Known compounds DTBZ and tetrabenazine (TBZ), as well as the presently identified HG-1 are shown as follows:

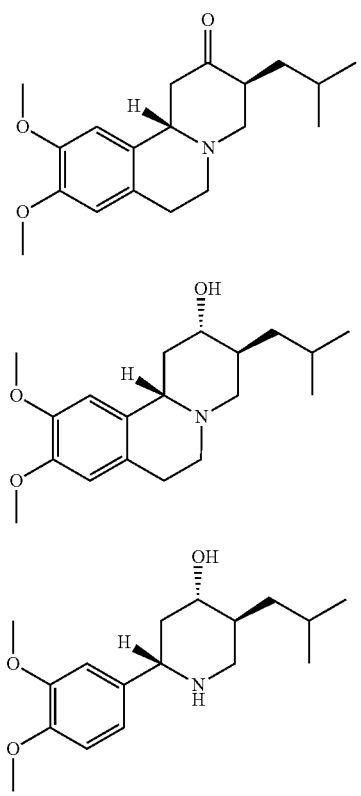

Several analogs of HG-1 were also designed and synthesized. A preliminary structure activity relationship (SAR) examination showed that various compounds having the dihydropyridone scaffold have improved glucose lowering effects as compared to effects shown for TBZ.

Racemic HG-2 which encompasses diastereomeric HG-1 shown above was synthesized according to Scheme 1 depicted below. As shown in Scheme 1, veratraldehyde 2 was treated with ammonium acetate and converted into β-amino acid 3 by condensation with malonic acid. Protection with Boc anhydride and subsequent condensation with potassium malonate methyl ester led to β-keto ester 4. Alkylation with isobutyl bromide in the presence of potassium carbonate afforded a mixture of compounds 5 and 6 (as identified in Scheme 1 below). The Boc group was removed and the mixture was treated with sodium bicarbonate in methanol to yield the cyclized compounds, compound 7 and HG-3. Compound 7 and HG-3 were isolated. Compound 7 was reduced with sodium borohydride to obtain HG-4 which was then converted to racemic HG-2 with lithium aluminum hydride. Diasteroisomers including compound HG-1 were isolated.

Scheme 1. Synthesis of Racemic HG-2:

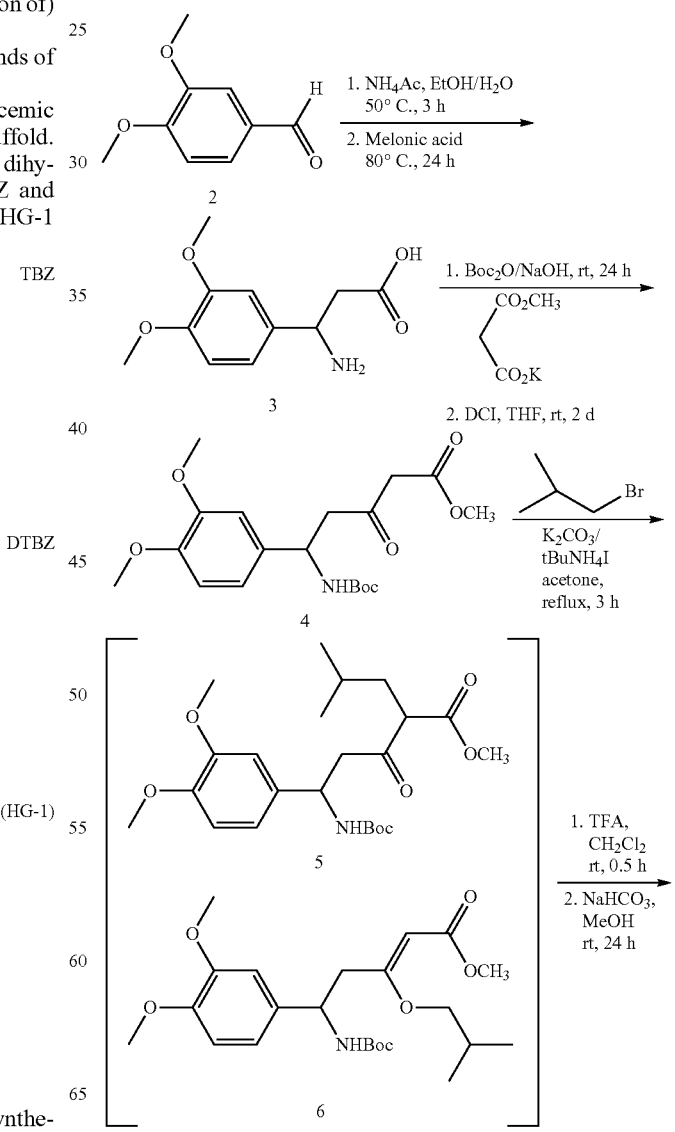

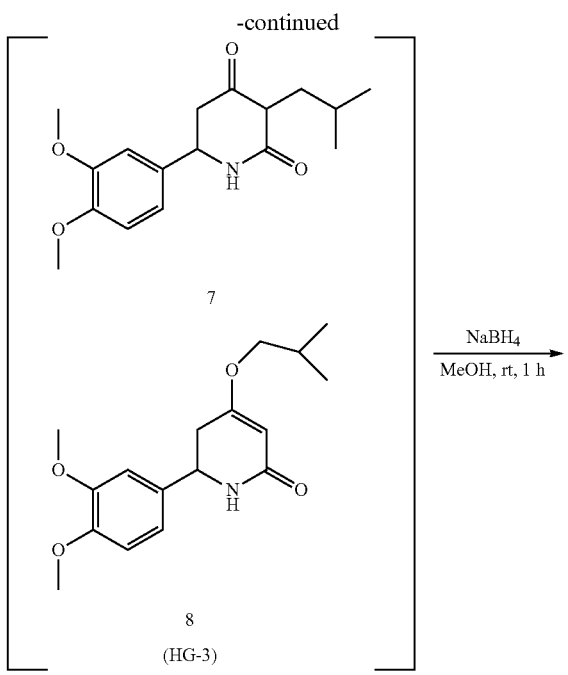

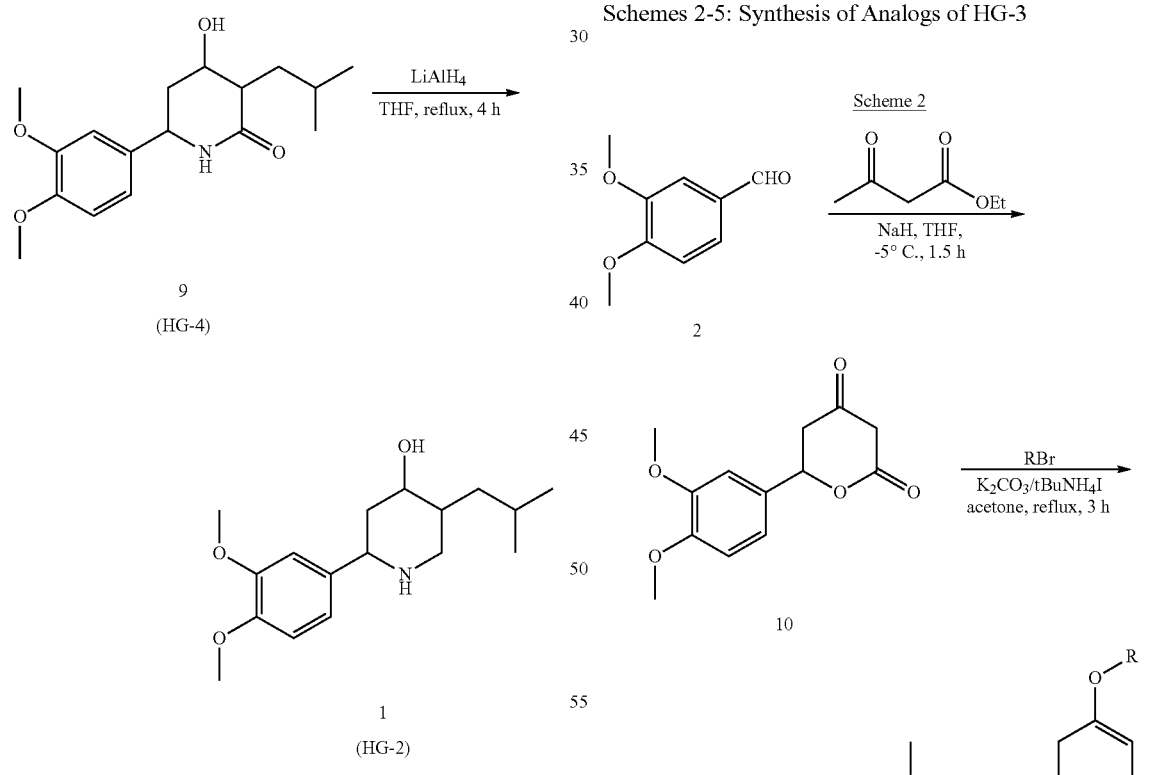

Figure 15:
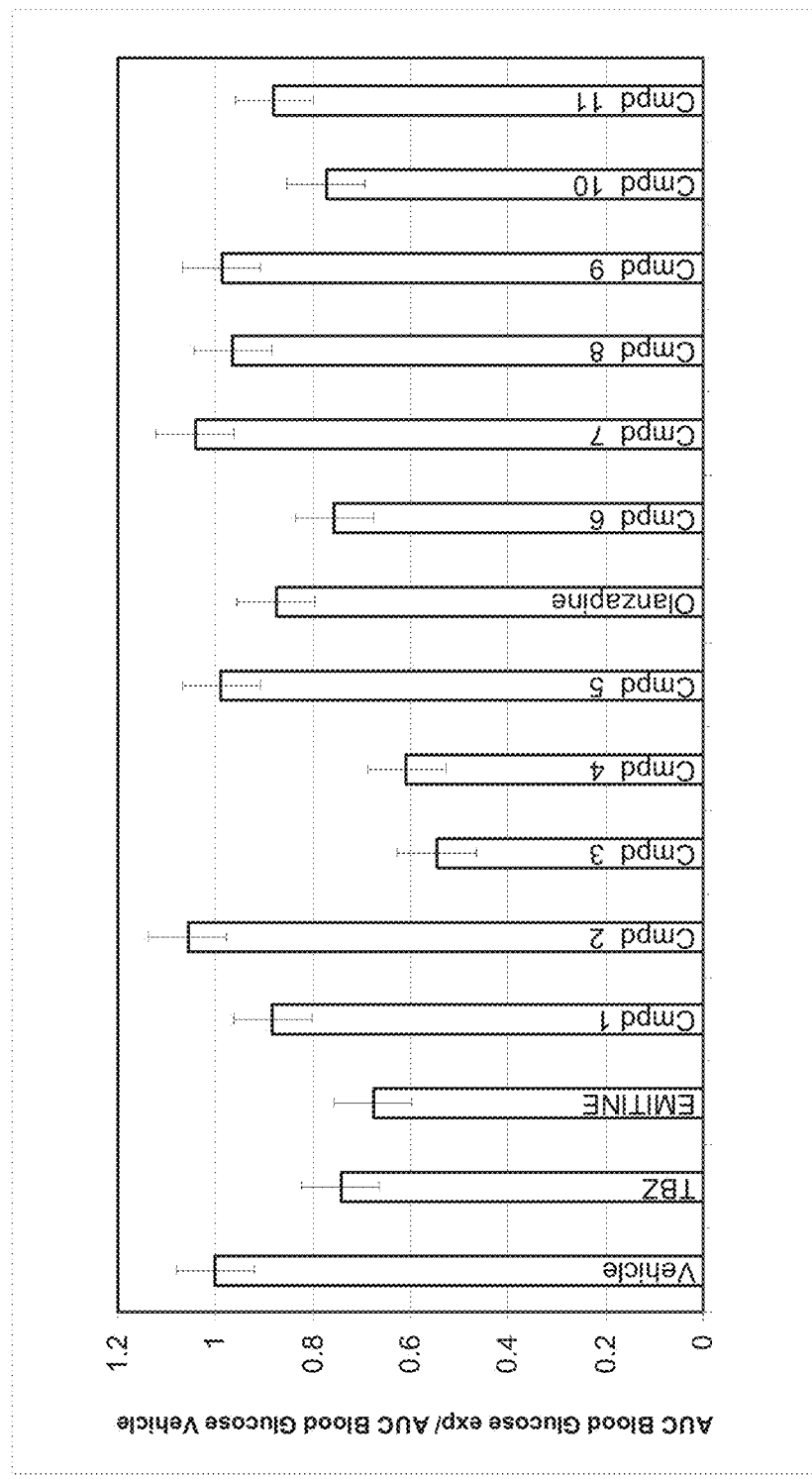
FIG. 15 is a bar graph showing the results of testing various analogs HG-1 to HG-11 in IPGTT glucose tolerance tests in rats. Results for TBZ, emetine, and olanzapine are also shown. Lewis rats fasted for 6 hours were administered the compounds orally (30 min, 2 mg/kg) followed by intraperitoneal glucose injection (0 min, 2 mg/kg), and plasma glucose levels were monitored for 120 mins. Results are presented as AUC percentage of the vehicle. Error bars indicate SEM (n=5).

FIG. 15, racemic HG-2 and diastereomer HG-1 were both less potent than TBZ, possibly due to diminished affinity for VMAT2.

During random screens of intermediates generated in the course of the synthesis of racemic HG-2 and diastereomer HG-1, however, it was surprisingly found that HG-3, a dihydropyridone which resulted from the competing O-versus C-alkylation of enolic β-keto ester 4 followed by cyclization, showed a potent hypoglycemic effect. As illustrated in FIG. 15, HG-3 decreased by 45% the AUC IPGTT (the area under the blood glucose concentration-time curve) at the dose of 2 mg/kg, as compared to a 26% decrease of the AUC IPGTT for TBZ. HG-3 showed a significant decrease in blood glucose levels as compared to TBZ.

In view of this result, several analogs of HG-3 were designed and synthesized. As outlined in Scheme 2 below, veratraldehyde 2 was condensed with ethyl acetoacetate and spontaneous cyclization yielded lactone 10. Using potassium carbonate as the base, O-alkylation of compound 10 with methyl bromide or isobutyl bromide provided HG-9 and HG-7. Similarly, as outlined in Scheme 3, HG-10 and HG-8 were prepared from dihydroisoquinoline 13 via condensation with dimethyl 1,3-acetonedicarboxylate followed by cyclization and alkylation. As shown in Scheme 4, DDQ-induced aromatization of HG-3 yielded compound 17. As shown in Scheme 5, acidic hydrolysis of HG-3 yielded HG-5.

Schemes 2-5: Synthesis of Analogs of HG-3

Racemic HG-2 and its diastereoisomer HG-1 were evaluated for their ability to improve glucose tolerance by performing intraperitoneal glucose tolerance tests (IPGTT) in rats. IPGTT testing is described above. See also Murthy, R., et al., *Eur. J. Nucl. Med. Mol. Imaging,* 2008, 35(4), 790-797.

FIG. 15 is a bar graph showing the results of testing various analogs in IPGTT glucose tolerance tests in rats. As seen in Scheme 3

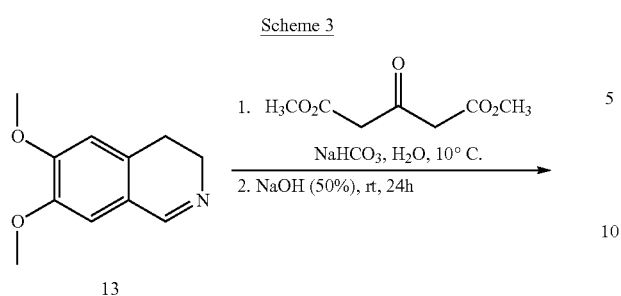

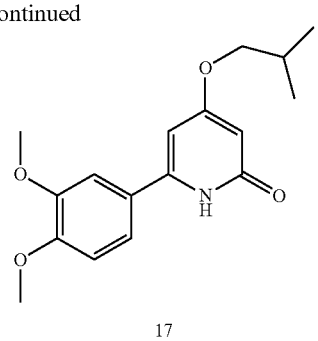

17

Scheme 5

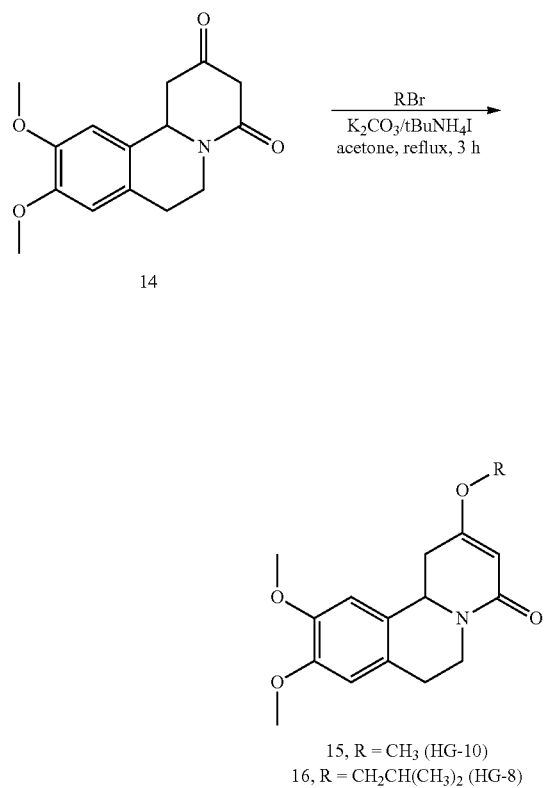

15, R = CH₃ (HG-10)
16, R = CH₂CH(CH₃)₂ (HG-8)

Scheme 4

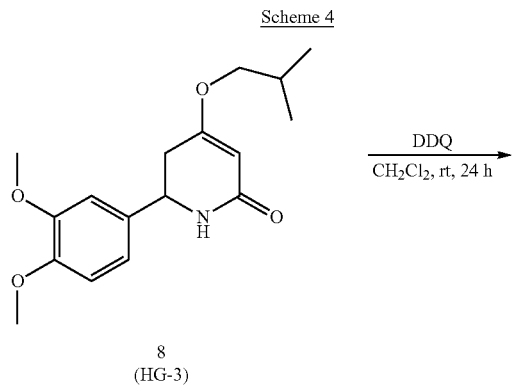

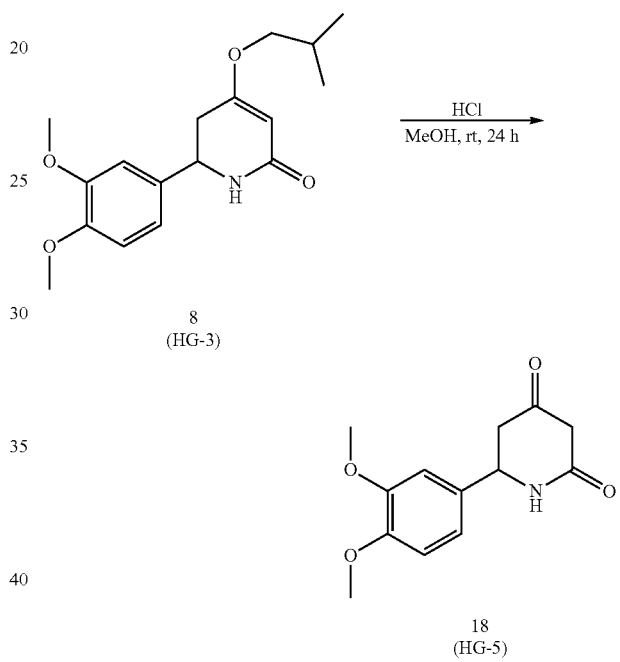

18
(HG-5)

Analogs prepared according to Schemes 2-5 above were tested for their hypoglycemic activities in rats using the IPGTT protocol. The results shown in FIG. 15 demonstrate that the dihydropyridone scaffold as in HG-3 is important to the improved hypoglycemic activity as compared to TBZ. Replacement of the dihydropyridone with dihydropyrone as in HG-9 and HG-7, and oxidation or hydrolysis of HG-3 as in compound 17 and HG-5 resulted in loss of the improved activity seen with HG-3. Interestingly, the rigid analogs, HG-10 and HG-8 were active but less potent than some of the analogs of HG-3.

Figure 16:
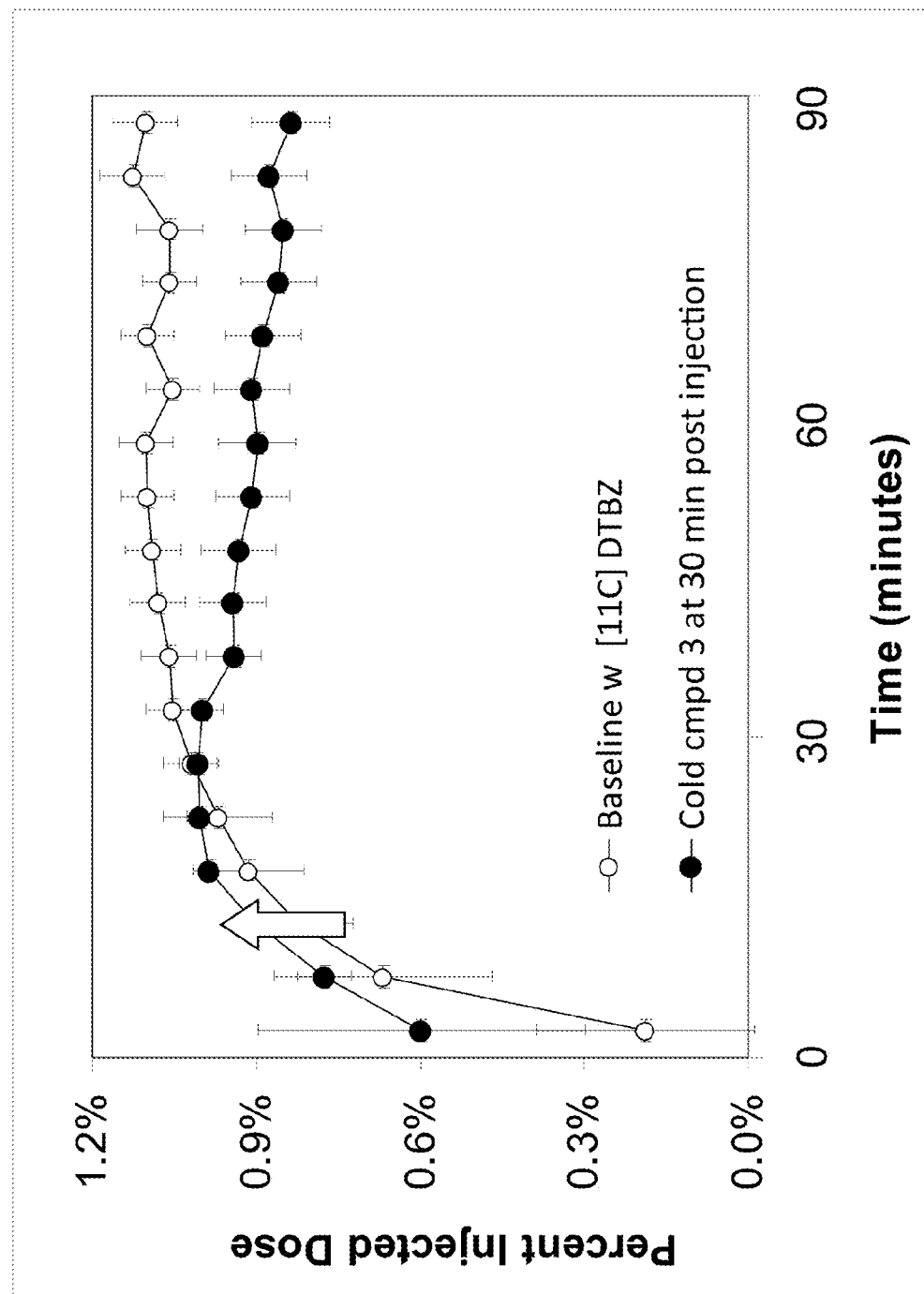
FIG. 16 shows the effect post injection of HG-3 on biodistribution of [$^{11}$C]DTBZ in the pancreas. PET scans were performed on anesthetized 12-14 week old Lewis male rats injected with radioligand [$^{11}$C]DTBZ (0 min, 0.5-1.0 μCi/gm body weight, specific activity >2000 mCi/mole) and cold compound 8 (HG-3) (30 mins, 2 mg/kg). The fraction of radioligand in the pancreas relative to the total amount injected was calculated and plotted versus time after injection. Error bars indicate SEM (n=3).

To determine whether the strong hypoglycemic effect of HG-3 is conferred by binding to VMAT2 in beta cells, a PET study was performed in rats. The animals were treated with radiolabeled DTBZ and the uptake of [$^{11}$C] DTBZ in the pancreas was monitored by PET scan in the presence of excess of HG-3. Contrary to expectations, HG-3 did not significantly displace [$^{11}$C]DTBZ in the endocrine pancreas (FIG. 16), suggesting a weak binding of HG-3 to VMAT2 relative to DTBZ. HG-4 also showed weak binding (data not shown).

DTBZ and its analogs are structurally similar to a class of quinolizine alkaloids previously shown to inhibit dipeptidyl peptidase IV (DDP-IV), Lubbers A, et al., *Biorg Med Chem Lett.* 2007, 17, 2966. To examine whether DDP-IV plays a role in the insulin enhancement seen with HG-3, the effect of HG-3 on DDP-IV was tested in vitro. HG-3 tested negative, however, against DDP-IV at concentrations up to 10 µM (data not shown). Therefore, the mechanism underlying the antihyperglycemic effect of HG-3 is not certain.

Example 4

Synthesis Examples

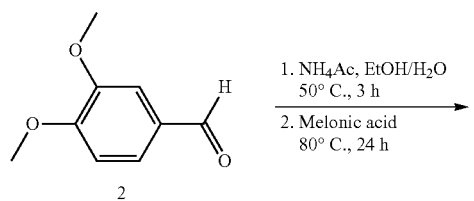

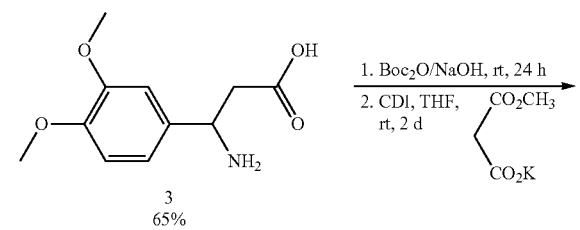

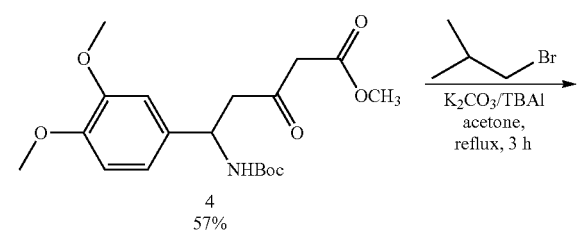

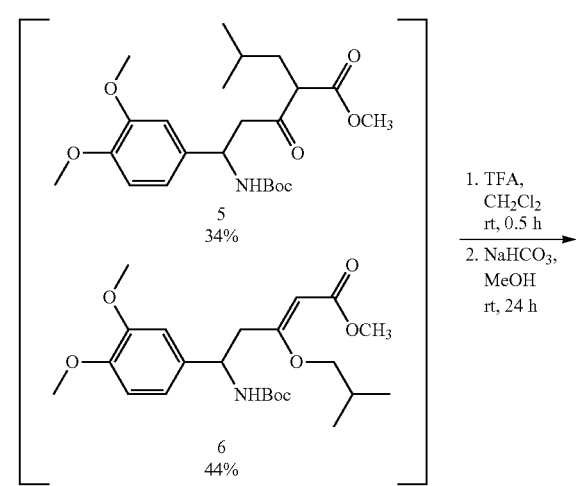

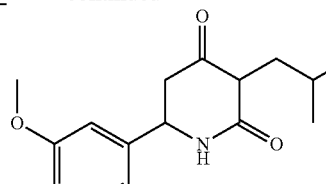

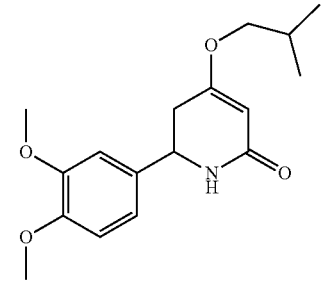

3-amino-3-(3,4-dimethoxyphenyl) propanoic acid (3)

3,4-dimethoxybenzaldehyde (50 g, 0.33 mol) and NH₄OAc (50 g) was mixed in EtOH (95%, 50 ml). The mixture was warmed up to 50° C. and to this solution, melonic acid (63 g, 0.6 mol) was added slowly followed by additional EtOH (95%, 25 ml). The reaction was then refluxed for 3 h and kept at 80° C. for 24 h. The precipitate was filtered, washed with EtOH and recrystalized in EtOH (50%) to give 47.8 g of the product 3 as white solid (yield: 65%). $^1$H NMR (300 MHz, D₂O): δ 6.90-6.87 (m, 3H), 4.44-4.39 (t, 1H), 3.69 (s, 3H), 3.67 (s, 3H), 2.76-2.57 (m, 2H). MS (EI) m/z: 226 (M$^+$+H).

Methyl 5-(tert-butoxycarbonylamino)-5-(3,4-dimethoxyphenyl)-3-oxopentanoate (4)

Compound 3 (5 g, 22.2 mmol) was dissolved in 1N NaOH (10 ml) and to this solution, Boc₂O (6 g, 27.5 mmol) was added in portion. The reaction was stirred at room temperature for 24 h and was quenched with KHSO₄ (20 g). The aqueous solution was extracted with ethyl acetate (100 ml) twice and the combined organics was dried over sodium sulfate. Removal of the solvent afforded 7 g of the crude product 3-(tert-butoxycarbonylamino)-3-(3,4-dimethoxyphenyl) propanoic acid (yield: 97%)

The product obtained above (5.6 g, 17.2 mmol) was dissolved in DMSO (20 ml) and to this solution, CDI (4 g, 24.7 mmol) was added in portion. The reaction was stirred at room temperature for 12 h. Potassium malonate methyl ester (4 g, 25.6 mmol) and anhydrous MgCl₂ (2 g, 21.1 mmol) was mixed in THF (15 ml). The mixture was heated at 50° C. for 24 h. After cooling down to room temperature, the solution was mixed with the imidazolide solution above and the reaction was stirred at room temperature for 2 d. The reaction was quenched with KHSO₄ (Saturated, 100 ml). The aqueous phase was extracted with ethyl acetate (100 ml) twice. The combined organics was washed with brine and dried over sodium sulfate. Removal of the solvent gave a yellow oil, which became solid after standing overnight. The crude product was recrystalized in EtOH to give 3.7 g of product 4 as yellow solid (yield: 57%). $^1$H NMR (300 MHz, CDCl$_3$): δ 6.82-6.81 (m, 3H), 5.25 (br, 1H), 5.05-5.01 (m, 1H), 3.87 (s, 3H), 3.85 (s, 3H), 3.72 (s, 3H), 3.40 (s, 2H), 3.20-3.00 (dd, 2H), 1.42 (s, 9H). MS (EI) m/z: 382 (M$^+$+H).

Synthesis of HG-3

6-(3,4-dimethoxyphenyl)-4-isobutoxy-5,6-dihydro-pyridin-2(1H)-one (HG-3)

With reference to Scheme 1, compound 4 (0.5 g, 1.3 mmol) and K$_2$CO$_3$ (0.5 g) was suspended in acetone (10 ml) followed by addition of TBAI (50 mg). To this mixture, isobutyl bromide (0.3 ml, 2.8 mmol) was added slowly. The reaction was refluxed for 3 h and quenched with water (50 ml). The aqueous phase was extracted with ethyl acetate (20 ml) twice. The combined organics was washed with brine and dried over sodium sulfate. Removal of the solvent gave a yellow oil residue, which was purified by chromatography on silica gel (elute with CH$_2$Cl$_2$/EtOAc 1:1) to give a mixture of compound 5 and 6 as light yellow oil (0.45 g, 78%).

The mixture obtained above was dissolved in CH$_2$Cl$_2$ (1 ml) and to this solution, TFA (1 ml) was added slowly. The reaction was stirred at room temperature for 0.5 h. After removing the solvent, the residue was re-dissolved in MeOH (5 ml) followed by addition of NaHCO$_3$ (1 g). After filtration, MeOH was removed under reduced pressure and the residue was separated by chromatography on silica gel (elute with CH$_2$Cl$_2$/EtOAc 1:1 first, and then EtOAc) to give compound 7 (0.14 g) and HG-3 (0.17 g) quantitatively. HG-3: $^1$H NMR (300 MHz, CDCl$_3$) δ 6.90-6.85 (m, 2H), 6.84 (s, 1H), 5.45 (br, 1H), 5.07 (s, 1H), 4.69-4.63 (dd, 1H), 3.87 (s, 3H), 3.86 (s, 3H), 3.64-3.60 (m, 2H), 2.71-2.47 (m, 2H), 2.02-1.96 (m, 1H), 0.96-0.93 (dd, 6H); $^{13}$C NMR (75 MHz, CD3OD) δ 170.0, 168.9, 149.4, 149.1, 133.5, 119.0, 111.4, 109.3, 93.8, 75.1, 56.3, 56.2, 55.0, 37.3, 28.1, 19.5, 19.4; ESI-MS (M$^+$+H): 306.

Synthesis of HG-4

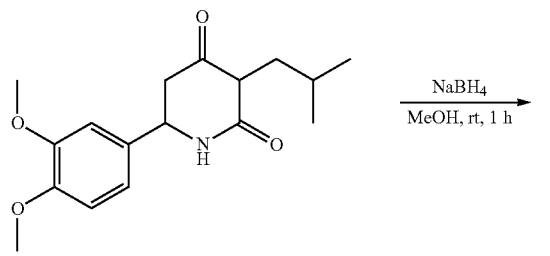

7

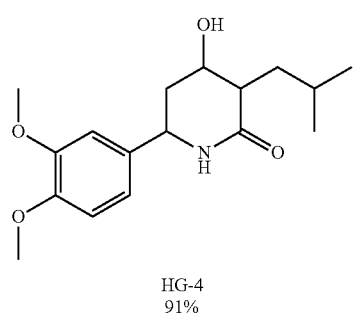

HG-4
91%

Compound 7 (0.14 g, 0.46 mmol) obtained above was dissolved in MeOH (5 ml) and to this solution, NaBH$_4$ (50 mg) was added in portion. After addition, the reaction was stirred at room temperature for 1 h. After removing solvent, the residue was suspended in water and the aqueous phase was extracted with CH$_2$Cl$_2$ (10 ml) twice. The combined organics was washed with brine and dried over sodium sulfate. The crude product was purified by chromatography on silica gel (elute with EtOAc first, and then EtOAc/MeOH 10:1) to give compound HG-4 and its diastereomers (0.13 g, 91%). HG-4: $^1$H NMR (300 MHz, CDCl$_3$) δ 6.85-6.79 (m, 3H), 5.78 (s, 1H), 4.49-4.44 (m, 1H), 4.29-4.26 (m, 1H), 3.87 (s, 3H), 3.86 (s, 3H), 2.60-2.55 (m, 1H), 2.30-2.24 (m, 1H), 2.04-1.85 (m, 3H), 1.66-1.61 (m, 1H), 0.98-0.95 (dd, 6H); $^{13}$C NMR (75 MHz, CD3OD) δ 174.8, 149.5, 148.9, 134.6, 118.6, 111.4, 109.3, 67.4, 56.3, 54.5, 44.9, 38.1, 35.7, 26.3, 23.3, 22.9; ESI-MS (M$^+$+H): 308.

Synthesis of Racemic HG-2 and Diastereomer HG-1

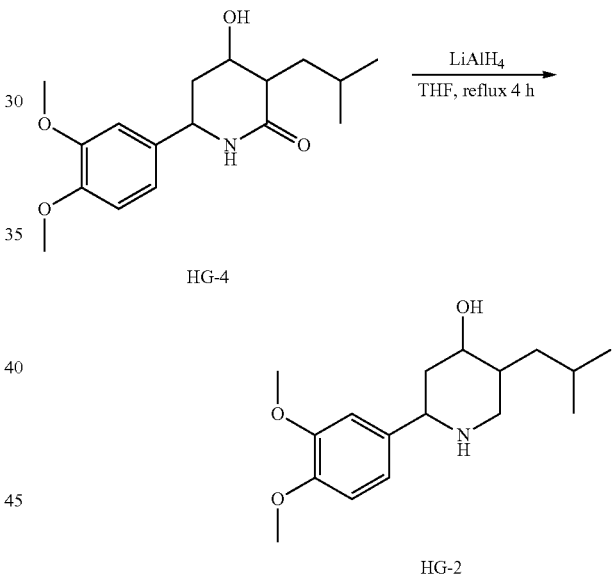

HG-4 or its diastereomers (20 mg, 0.065 mmol) was dissolved in THF (2 ml) and to this solution, LiAlH$_4$ (100 mg) was added in portion. The reaction was refluxed for 4 h and quenched 1N NaOH (5 ml). The mixture was passed through a celite pat and washed with CH$_2$Cl$_2$. The organic phase was washed with brine and dried over sodium sulfate. The crude product was purified by chromatography on silica gel (elute with EtOAc first, and then EtOAc/MeOH 10:1) to give racemic HG-2 and its diastereomer HG-1 (14 mg, 74%). HG-1: $^1$H NMR (300 MHz, CDCl$_3$) δ 6.93-6.78 (m, 3H), 3.95-3.89 (m, 1H), 3.87 (s, 3H), 3.86 (s, 3H), 3.62-3.58 (dd, 1H), 3.11-3.06 (dd, 1H), 2.83-2.78 (dd, 1H), 1.88-1.82 (m, 3H), 1.68-1.63 (m, 2H), 1.27-1.23 (m, 1H), 0.99-0.89 (dd, 6H); $^{13}$C NMR (75 MHz, CD3OD) δ 149.0, 148.3, 136.8, 118.7, 111.1, 110.2, 72.2, 60.2, 56.2, 56.1, 48.5, 38.6, 37.9, 32.7, 26.5, 24.4, 22.3. ESI-MS (M$^+$+H): 294.

Synthesis of HG-6

Figure 11:
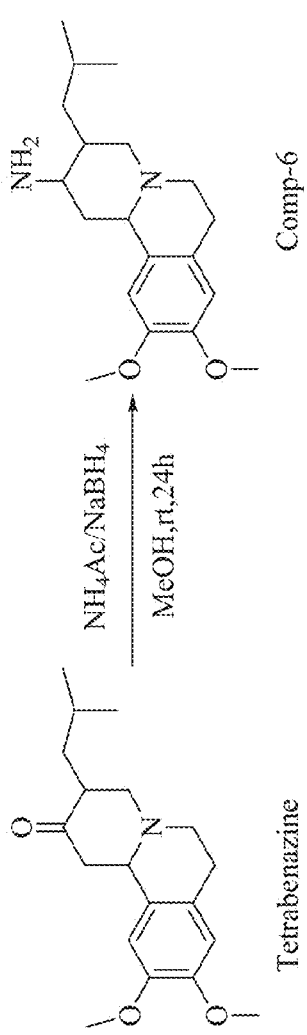
FIG. 11. A diagram showing synthetic schemes for HG-6.
Figure 11:
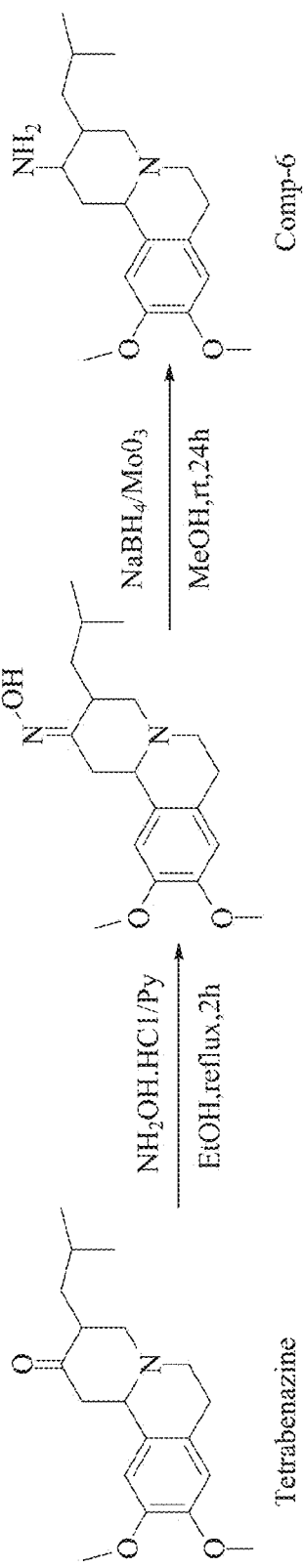

3-isobutyl-9,10-dimethoxy-2,3,4,6,7,11b-hexahydro-1H-pyrido[2,1-a]isoquinolin-2-amine Synthetic schematics are provided in FIG. 11.

With reference to FIG. 11, tetrabenazine (317 mg, 1 mmol) was dissolved in methanol (MeOH, 10 ml) and cooled with ice-water. To this solution, ammonia acetate (500 mg) was added, followed by the addition of sodium borohydride (50 mg) in portion. The reaction was stirred at room temperature for 24 hours and quenched with water. The aqueous solution was extracted with methylene chloride (10 ml) twice. The combined organic phase was washed with brine and dried with sodium sulfate. After removing the solvent, the residue was purified by chromatography. One hundred and fifty milligrams of (HG-6) (3-isobutyl-9,10-dimethoxy-2,3,4,6,7,11b-hexahydro-1H-pyrido[2,1-a]isoquinolin-2-amine) was obtained as white solid (yield: 47%).

HG-6 was also synthesized using the following alternative method: tetrabenazine (317 mg, 1 mmol) was dissolved in ethanol (EtOH, 10 ml) and hydroxylamine hydrochloride (70 mg, 1 mmol) was added, followed by the addition of pyridine (1 ml). The reaction was refluxed for 2 hours. After removing solvent, the residue was redissolved in methanol (MeOH, 10 ml). To this solution, $MoO_3$ (80 mg) and sodium borohydride (80 mg) were slowly added. The reaction was stirred at room temperature for 24 hours and quenched with water. The aqueous solution was extracted with methylene chloride (10 ml) twice. The combined organic phase was washed with brine and dried with sodium sulfate. After removing solvent, the residue was purified by chromatography. Two hundred and fifty milligrams of HG-6 (3-isobutyl-9,10-dimethoxy-2,3,4,6,7,11b-hexahydro-1H-pyrido[2,1-a]isoquinolin-2-amine) was obtained as white solid (yield: 78%).

Synthesis of HG-11

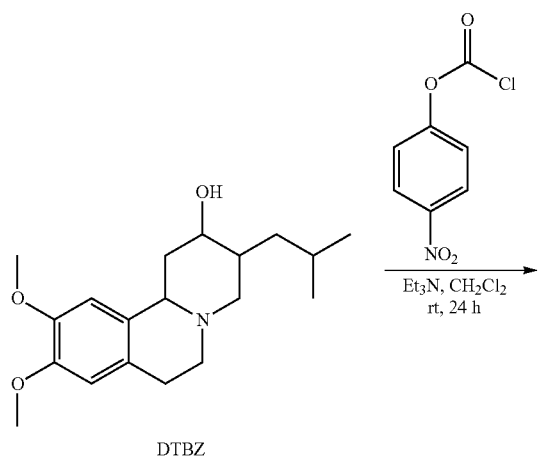

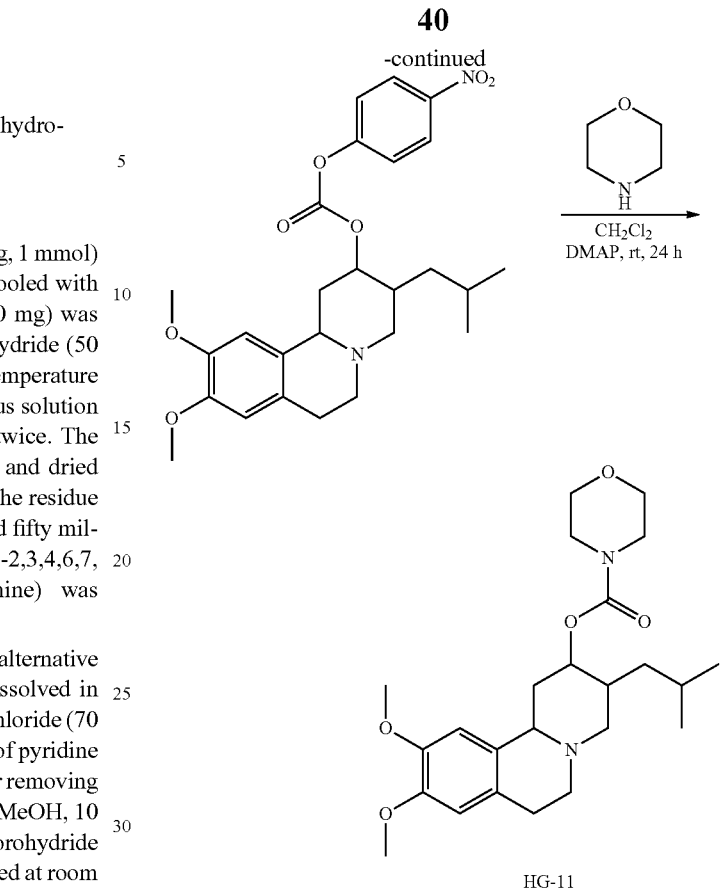

HG-11

DTBZ (100 mg, 0.31 mmol) was dissolved in $CH_2Cl_2$ (10 ml) and to this solution, 4-nitrophenyl carbonochloridate (62.5 mg, 0.31 mmol) was added in portions followed by addition of $Et_3N$ (0.1 ml). The reaction was stirred at room temperature for 24 h. After removing the solvent, the residue was purified by chromatography on silica gel (elute with EtOAc) to give the product as yellow solid.

The product obtained above was re-dissolved in $CH_2Cl_2$ (10 ml) and to this solution, morpholine (0.1 ml) was added slowly followed by addition of a catalytic amount of DMAP. The reaction was stirred at room temperature for 24 h. After removing solvent and excessive morpholine, the residue was purified by chromatography on silica gel (elute with EtOAc/$CH_2Cl_2$ 1:1 first, and the with EtOAc) to provide the product HG-11 as white solid (91 mg, 68%). $^1$H NMR (300 MHz, $CDCl_3$) δ 6.62 (s, 1H), 6.56 (s, 1H), 4.62-4.55 (m, 1H), 3.82 (d, 6H), 3.66 (m, 4H), 3.48 (m, 4H), 3.30 (m, 1H), 3.11-3.03 (m, 2H), 2.67-2.63 (m, 2H), 2.50 (m, 1H), 2.10 (m, 1H), 1.70-1.50 (m, 2H), 1.30-1.24 (m, 1H), 1.10-1.05 (m, 1H), 0.91-0.87 (t, 6H). $^{13}$C NMR (75 MHz, CD3OD) δ 155.4, 147.8, 147.5, 126.2, 115.9, 111.6, 108.2, 66.9, 60.9, 60.3, 56.4, 56.2, 52.0, 44.4, 40.0, 38.7, 37.4, 29.2, 25.9, 24.2, 22.4.

Pending application PCT/US08/03338 entitled Methods and Compositions for Modulating Insulin Secretion and Glucose Metabolism, which was filed on Mar. 12, 2008, and U.S. Provisional Application Ser. No. 60/906,623, filed on Mar. 12, 2007, and U.S. Provisional Application Ser. No. 60/932,810, filed May 31, 2007, are incorporated herein by reference in their entireties for all purposes.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound of formula I:

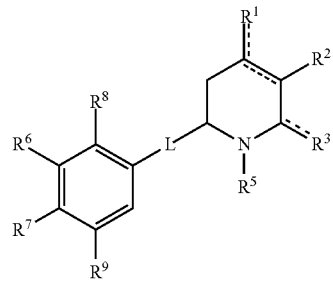

wherein
$R^1$ is $XR^4$ or O;
$R^2$ is H or $C_1$-$C_8$ alkyl;
$R^3$ is H or O;
X is O, S, NH or $CH_2$;
$R^4$ is H or $C_1$-$C_8$ alkyl;
$R^5$ is selected from the group consisting of H and $C_1$-$C_8$ alkyl, amine, $C_1$-$C_8$ alkylamine, acyl, and amide;
---- is an optional double bond,
L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;
$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;
$R^8$ and $R^9$ are each independently selected from the group consisting of H, $C_1$-$C_8$ alkyl, $C_1$-$C_8$ alkoxy, amine, $C_1$-$C_8$ alkylamine, and halo; and
when one of R' or $R^3$ is O, then the other is not O;
when ---- is not present between ring carbons, $R^2$ is other than H;
or an enantiomer, optical isomer, diastereomer, N-oxide, crystalline form, hydrate, or pharmaceutically acceptable salt thereof.

2. The compound of claim 1 wherein R' is $XR^4$.

3. The compound of claim 2 wherein $R^4$ is H or $C_1$-$C_4$ alkyl.

4. The compound of claim 1 wherein $R^2$ is H or $C_1$-$C_4$ alkyl.

5. The compound of claim 1 wherein X is O.

6. The compound of claim 1 wherein L is a bond.

7. The compound of claim 1 wherein $R^6$ and $R^7$ are each independently selected from the group consisting of $OCH_3$, $NH_2$, and Cl.

8. The compound of claim 7 wherein $R^6$ and $R^7$ are both $OCH_3$.

9. The compound of claim 1 wherein $R^8$ and $R^9$ are both H.

10. The compound of claim 1 which is selected from the group consisting of:

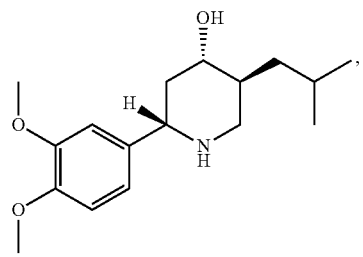

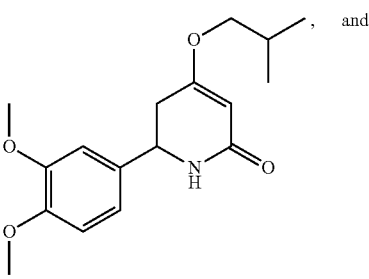

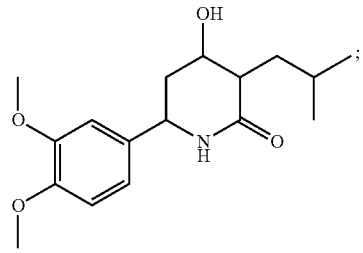

or an enantiomer, optical isomer, diastereomer, N-oxide, crystalline form, hydrate, or pharmaceutically acceptable salt thereof.

11. The compound of claim 10 which is selected from the group consisting of:

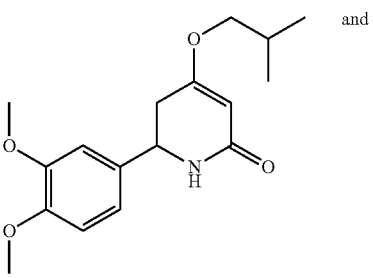

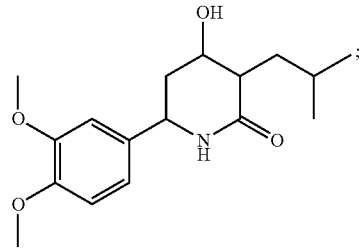

or an enantiomer, optical isomer, diastereomer, N-oxide, crystalline form, hydrate, or pharmaceutically acceptable salt thereof.

12. A compound of the formula II:

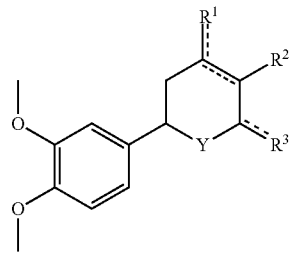

wherein
Y is NH or O;
$R^1$ is $XR^4$ or O;
$R^2$ is H or $C_1$-$C_8$ alkyl;
$R^3$ is H or O;
X is NH or O;
$R^4$ is H, $C_1$-$C_8$ alkyl, C(=O)-heterocyclic; and
----- is an optional double bond;
with the proviso that the compound is not:

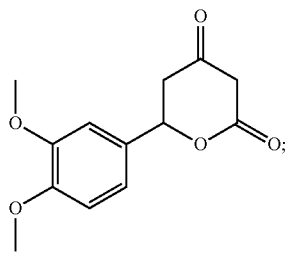 [SMILES: COc1ccc(C2CC(=O)CC(=O)O2)cc1OC]

or an enantiomer, optical isomer, diastereomer, N-oxide, crystalline form, hydrate, or pharmaceutically acceptable salt thereof.

13. The compound of claim 12 wherein
Y is NH or O;
$R^1$ is $XR^4$ or O;
$R^2$ is H or $C_1$-$C_8$ alkyl;
X is O;
$R^4$ is H or $C_1$-$C_8$ alkyl; and
----- is an optional double bond.

14. The compound of claim 13 wherein Y is NH.

15. The compound of claim 14 which is selected from the group consisting of:

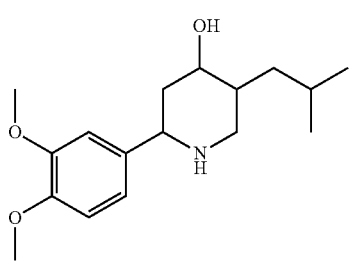

HG-2 and

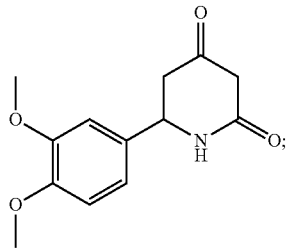

HG-5 or an enantiomer, optical isomer, diastereomer, N-oxide, crystalline form, hydrate, or pharmaceutically acceptable salt thereof.

16. The compound of claim 13 wherein Y is O.

17. The compound of claim 16 which is selected from the group consisting of:

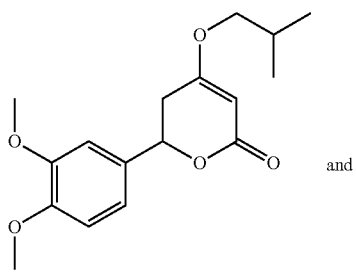

HG-7 and

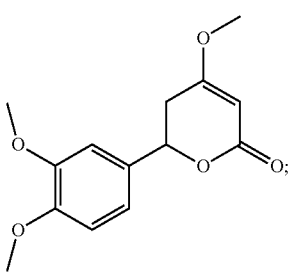

HG-9 or an enantiomer, optical isomer, diastereomer, N-oxide, crystalline form, hydrate, or pharmaceutically acceptable salt thereof.

18. A compound which is selected from the group consisting of:

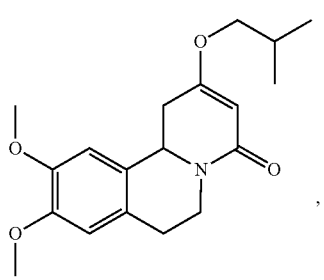

HG-8

,

-continued

HG-11
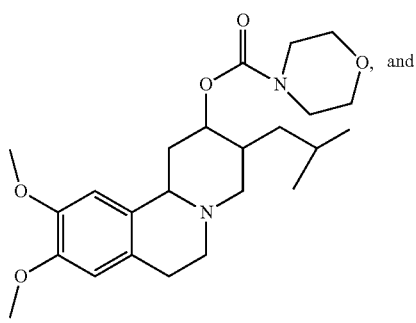

HG-6
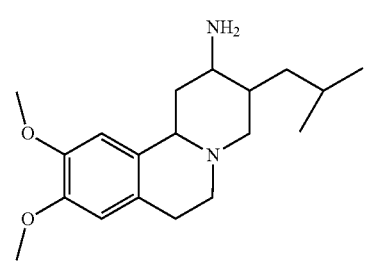

or an enantiomer, optical isomer, diastereomer, N-oxide, crystalline form, hydrate, or pharmaceutically acceptable salt thereof.

19. A pharmaceutical composition comprising a compound of formula I:

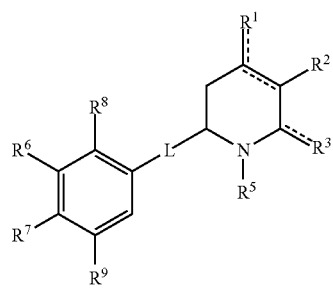

wherein
R¹ is XR⁴ or O;
R² is H or $C_1$-$C_8$ alkyl;
R³ is H or O;
X is O, S, NH or $CH_2$;
R⁴ is H or $C_1$-$C_8$ alkyl;
R⁵ is selected from the group consisting of H and $C_1$-$C_8$ alkyl, amine, $C_1$-$C_8$ alkylamine, acyl, and amide;
----- is an optional double bond;
L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;
R⁶ and R⁷ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;
R⁸ and R⁹ are each independently selected from the group consisting of H, $C_1$-$C_8$ alkyl, $C_1$-$C_8$ alkoxy, amine, $C_1$-$C_8$ alkylamine, and halo; and
when one of R¹ or R³ is O, then the other is not O;
when ---- is not present between ring carbons, R² is other than H;
or an enantiomer, optical isomer, diastereomer, N-oxide, crystalline form, hydrate, or pharmaceutically acceptable salt thereof;
and a pharmaceutically acceptable carrier.

20. The pharmaceutical composition of claim 19 wherein R¹ is XR⁴.
21. The pharmaceutical composition of claim 20 wherein R⁴ is H or $C_1$-$C_4$ alkyl.
22. The pharmaceutical composition of claim 19 wherein R² is H or $C_1$-$C_4$ alkyl.
23. The pharmaceutical composition of claim 19 wherein X is O.
24. The pharmaceutical composition of claim 19 wherein L is a bond.
25. The pharmaceutical composition of claim 19 wherein R⁶ and R⁷ are each independently selected from the group consisting of $OCH_3$, $NH_2$, and Cl.
26. The pharmaceutical composition of claim 25 wherein R⁶ and R⁷ are both $OCH_3$.
27. The pharmaceutical composition of claim 19 wherein R⁸ and R⁹ are both H.
28. The pharmaceutical composition of claim 19 wherein the compound is selected from the group consisting of:

HG-1
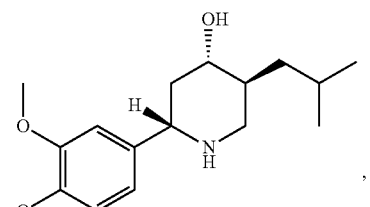

HG-3
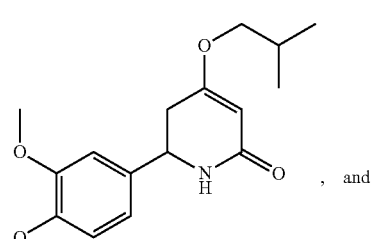

HG-4
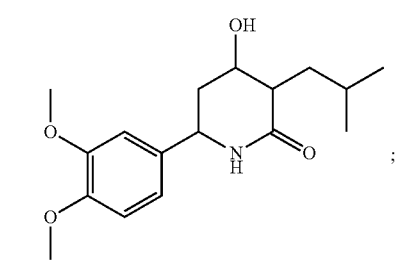

or an enantiomer, optical isomer, diastereomer, N-oxide, crystalline form, hydrate, or pharmaceutically acceptable salt thereof;
and a pharmaceutically acceptable carrier.

29. The pharmaceutical composition of claim 28 wherein the compound is selected from the group consisting of:

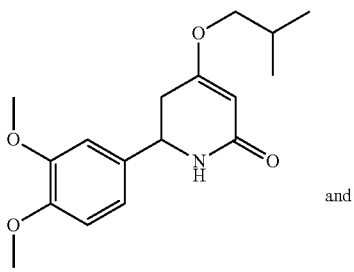
HG-3

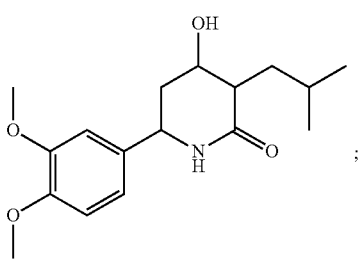
HG-4 or an enantiomer, optical isomer, diastereomer, N-oxide, crystalline form, hydrate, or pharmaceutically acceptable salt thereof;
and a pharmaceutically acceptable carrier.

30. A pharmaceutical composition comprising a compound of formula II:

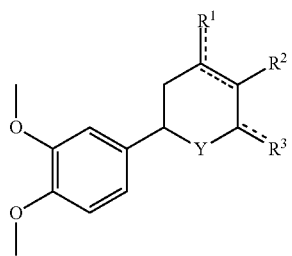
II wherein
Y is NH or O;
$R^1$ is $XR^4$ or O;
$R^2$ is H or $C_1$-$C_8$ alkyl;
$R^3$ is H or O;
X is NH or O;
$R^4$ is H, $C_1$-$C_8$ alkyl, C(=O)-heterocyclic; and
----- is an optional double bond;
with the proviso that the compound is not:

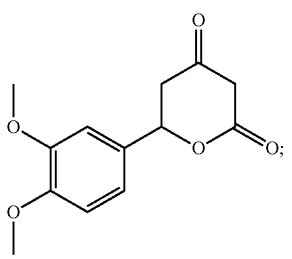 [SMILES: COc1ccc(C2CC(=O)CC(=O)O2)cc1OC]

or an enantiomer, optical isomer, diastereomer, N-oxide, crystalline form, hydrate, or pharmaceutically acceptable salt thereof;

and a pharmaceutically acceptable carrier.

31. The pharmaceutical composition of claim 30 wherein
Y is NH or O;
R' is $XR^4$ or O;
$R^2$ is H or $C_1$-$C_8$ alkyl;
X is O;
$R^4$ is H or $C_1$-$C_8$ alkyl; and
----- is an optional double bond.

32. The pharmaceutical composition of claim 31 wherein Y is NH.

33. The pharmaceutical composition of claim 32 wherein the compound is selected from the group consisting of:

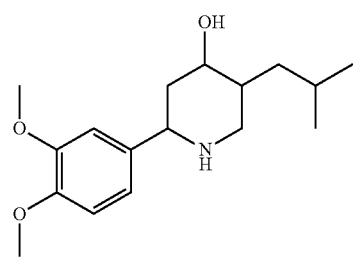
HG-2 and

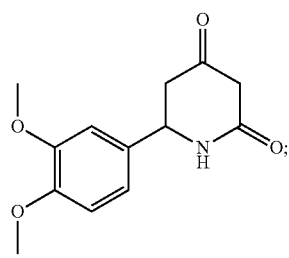
HG-5 or an enantiomer, optical isomer, diastereomer, N-oxide, crystalline form, hydrate, or pharmaceutically acceptable salt thereof;

and a pharmaceutically acceptable carrier.

34. The pharmaceutical composition of claim 31 wherein Y is O.

35. The pharmaceutical composition of claim 34 wherein the compound is selected from the group consisting of:

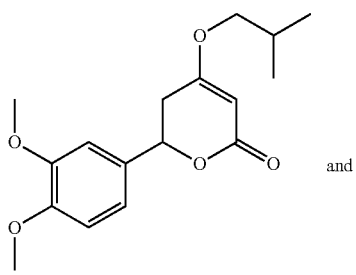
HG-7 and

-continued

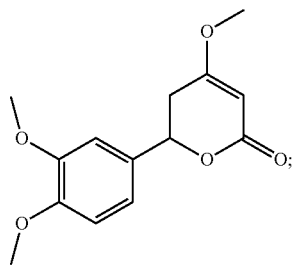
HG-9 or an enantiomer, optical isomer, diastereomer, N-oxide, crystalline form, hydrate, or pharmaceutically acceptable salt thereof;

and a pharmaceutically acceptable carrier.

36. A pharmaceutical composition which comprises a compound which is selected from the group consisting of:

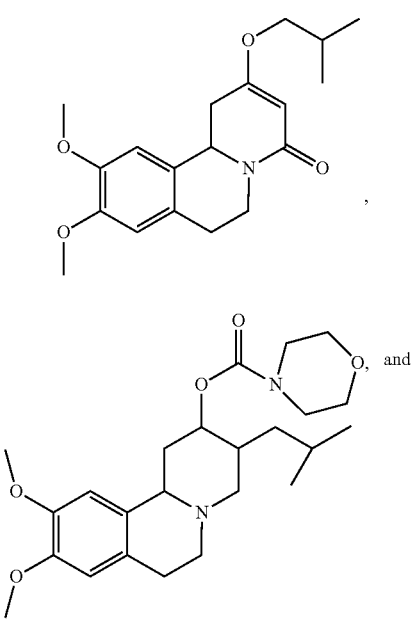

HG-8

HG-11

HG-6 or an enantiomer, optical isomer, diastereomer, N-oxide, crystalline form, hydrate, or pharmaceutically acceptable salt thereof;

and a pharmaceutically acceptable carrier.

37. A method of treatment or prevention of diabetes or hyperglycemia which comprises administering to a patient in need thereof an effective amount of a compound of formula I

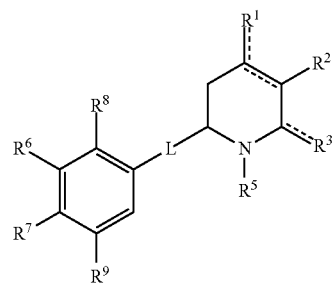
I wherein
$R^1$ is $XR^4$ or O;
$R^2$ is H or $C_1$-$C_8$ alkyl;
$R^3$ is H or O;
X is O, S, NH or $CH_2$;
$R^4$ is H or $C_1$-$C_8$ alkyl;
$R^5$ is selected from the group consisting of H and $C_1$-$C_8$ alkyl, amine, $C_1$-$C_8$ alkylamine, acyl, and amide;
----- is an optional double bond,
L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;
$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;
$R^8$ and $R^9$ are each independently selected from the group consisting of H, $C_1$-$C_8$ alkyl, $C_1$-$C_8$ alkoxy, amine, $C_1$-$C_8$ alkylamine, and halo; and
when one of R' or $R^3$ is O, then the other is not O;
when ---- is not present between ring carbons, $R^2$ is other than H;
or an enantiomer, optical isomer, diastereomer, N-oxide, crystalline form, hydrate, or pharmaceutically acceptable salt thereof.

38. A method of normalizing blood glucose levels which comprises administering to a subject in need thereof an effective amount of a compound of formula I

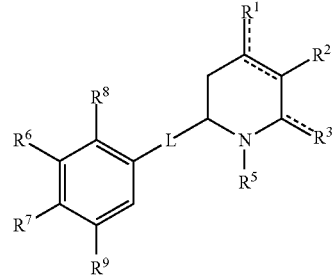
I wherein
$R^1$ is $XR^4$ or O;
$R^2$ is H or $C_1$-$C_8$ alkyl;
$R^3$ is H or O;
X is O, S, NH or $CH_2$;
$R^4$ is H or $C_1$-$C_8$ alkyl;

$R^5$ is selected from the group consisting of H and $C_1$-$C_8$ alkyl, amine, $C_1$-$C_8$ alkylamine, acyl, and amide, ---- is an optional double bond, L is selected from the group consisting of a bond, NH, S, O, and divalent $C_1$-$C_8$ alkyl, $C_1$-$C_8$ alkoxy, ether, $C_1$-$C_8$ alkylamine, thioalkyl, and thioether;

$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl;

$R^8$ and $R^9$ are each independently selected from the group consisting of H, $C_1$-$C_8$ alkyl, $C_1$-$C_8$ alkoxy, amine, $C_1$-$C_8$ alkylamine, and halo; and when one of R' or $R^3$ is O, then the other is not O;

when ---- is not present between ring carbons, $R^2$ is other than H;

or an enantiomer, optical isomer, diastereomer, N-oxide, crystalline form, hydrate, or pharmaceutically acceptable salt thereof.

39. The method of claim 37 or 38 wherein R' is $XR^4$.

40. The method of claim 39 wherein $R^4$ is H or $C_1$-$C_4$ alkyl.

41. The method of claim 37 or 38 wherein $R^2$ is H or $C_1$-$C_4$ alkyl.

42. The method of claim 37 or 38 wherein X is O.

43. The method of claim 37 or 38 wherein L is a bond.

44. The method of claim 37 or 38 wherein $R^6$ and $R^7$ are each independently selected from the group consisting of $OCH_3$, $NH_2$, and Cl.

45. The method of claim 44 wherein $R^6$ and $R^7$ are both $OCH_3$.

46. The method of claim 37 or 38 wherein $R^8$ and $R^9$ are both H.

47. The method of claim 37 or 38 wherein the compound is selected from the group consisting of:

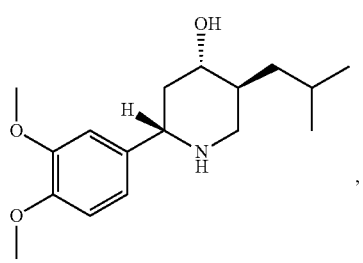

HG-1

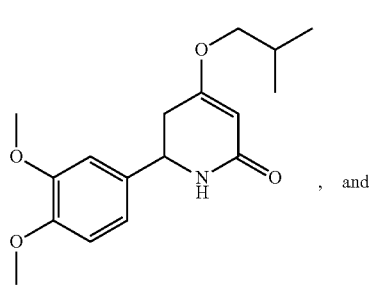

HG-3

, and

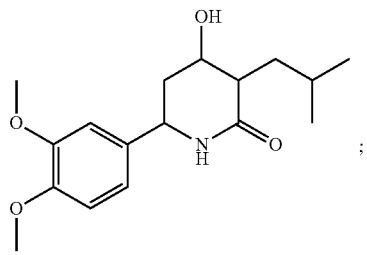

HG-4

;

or an enantiomer, optical isomer, diastereomer, N-oxide, crystalline form, hydrate, or pharmaceutically acceptable salt thereof.

48. The method of claim 47 wherein the compound is selected from the group consisting of:

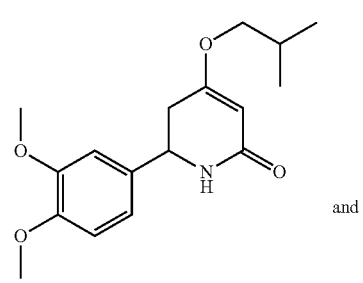

HG-3 and

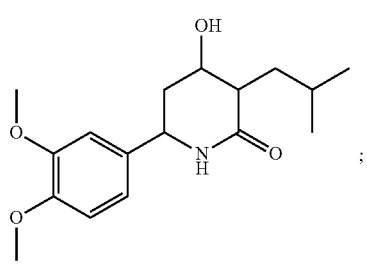

HG-4

;

or an enantiomer, optical isomer, diastereomer, N-oxide, crystalline form, hydrate, or pharmaceutically acceptable salt thereof.

49. A method of treatment or prevention of diabetes or hyperglycemia which comprises administering to a patient in need thereof an effective amount of a compound of formula II:

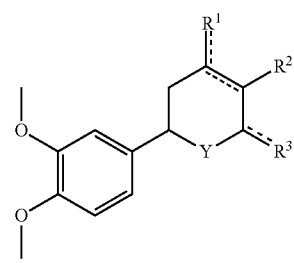

II wherein
Y is NH or O;
$R^1$ is $XR^4$ or O;
$R^2$ is H or $C_1$-$C_8$ alkyl;

R³ is H or O;

X is NH or O;

R⁴ is H, $C_1$-$C_8$ alkyl, C(=O)-heterocyclic; and

----- is an optional double bond;

or an enantiomer, optical isomer, diastereomer, N-oxide, crystalline form, hydrate, or pharmaceutically acceptable salt thereof.

50. A method of normalizing blood glucose levels which comprises administering to a subject in need thereof an effective amount of a compound of formula II:

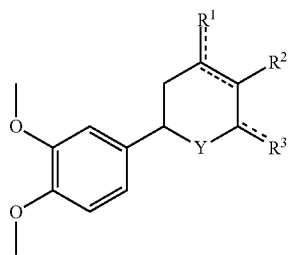

wherein

Y is NH or O;

R¹ is XR⁴ or O;

R² is H or $C_1$-$C_8$ alkyl;

R³ is H or O;

X is NH or O;

R⁴ is H, $C_1$-$C_8$ alkyl, C(=O)-heterocyclic; and

----- is an optional double bond;

or an enantiomer, optical isomer, diastereomer, N-oxide, crystalline form, hydrate, or pharmaceutically acceptable salt thereof.

51. The method of claim 49 or 50 wherein

Y is NH or O;

R' is XR⁴ or O;

R² is H or $C_1$-$C_8$ alkyl;

X is O;

R⁴ is H or $C_1$-$C_8$ alkyl; and

----- is an optional double bond.

52. The method of claim 51 wherein Y is NH.

53. The method of claim 52 wherein the compound is selected from the group consisting of:

HG-2

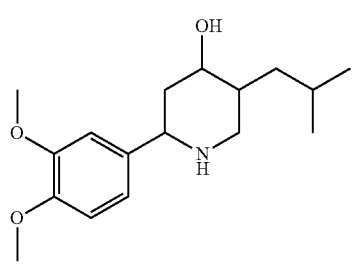

and

HG-5

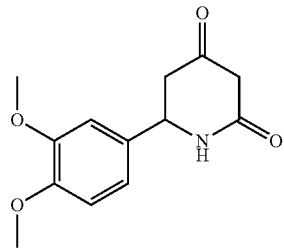

or an enantiomer, optical isomer, diastereomer, N-oxide, crystalline form, hydrate, or pharmaceutically acceptable salt thereof.

54. The method of claim 53 wherein Y is O.

55. The method of claim 54 wherein the compound is selected from the group consisting of:

HG-7

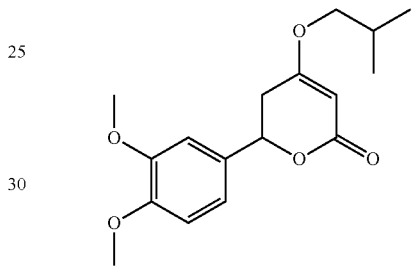

and

HG-9

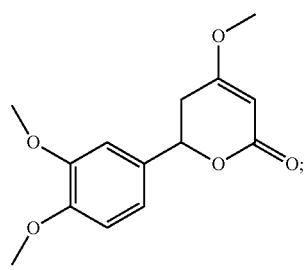

or an enantiomer, optical isomer, diastereomer, N-oxide, crystalline form, hydrate, or pharmaceutically acceptable salt thereof.

56. A method of treatment or prevention of diabetes or hyperglycemia which comprises administering to a patient in need thereof an effective amount of a compound selected from the group consisting of:

HG-8

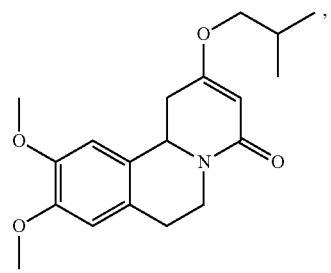

-continued

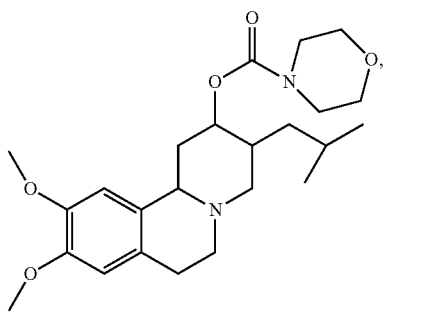
HG-11

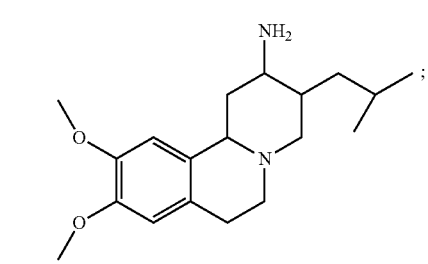
HG-6 or an enantiomer, optical isomer, diastereomer, N-oxide, crystalline form, hydrate, or pharmaceutically acceptable salt thereof.

57. A method of normalizing blood glucose levels which comprises administering to a subject in need thereof an effective amount of a compound selected from the group consisting of:

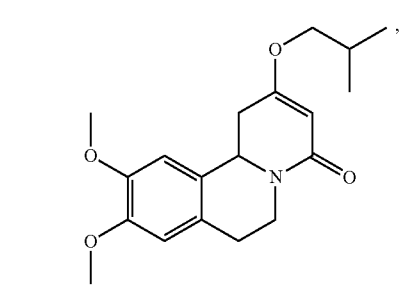
HG-8

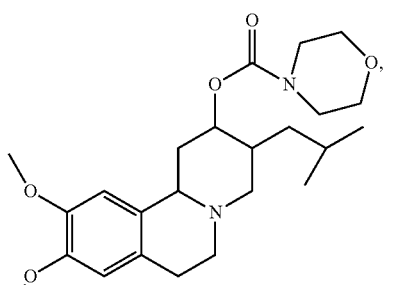
HG-11

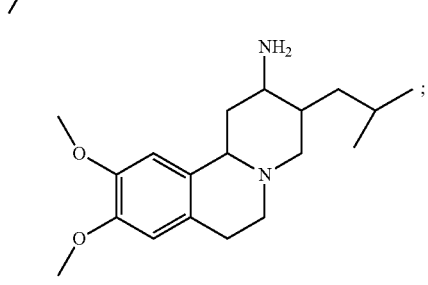
HG-6 or an enantiomer, optical isomer, diastereomer, N-oxide, crystalline form, hydrate, or pharmaceutically acceptable salt thereof.

58. The method of claim 56 or 57 wherein the compound is selected from the group consisting of:

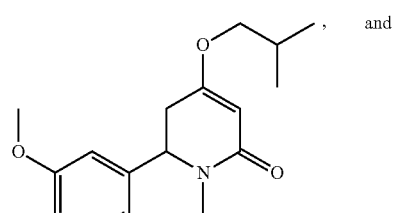
HG-8

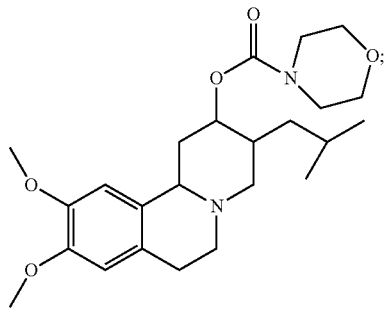
HG-11 or an enantiomer, optical isomer, diastereomer, N-oxide, crystalline form, hydrate, or pharmaceutically acceptable salt thereof.

59. A pharmaceutical composition comprising a compound of formula III:

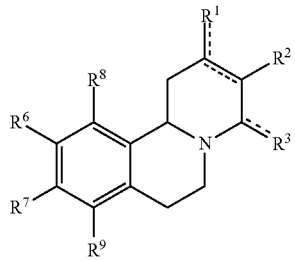
III wherein
$R^1$ is $XR^4$ or O;
$R^2$ is H or $C_1$-$C_8$ alkyl;
$R^3$ is H or O;
X is O, S, NH or $CH_2$;
$R^4$ is H, $C_1$-$C_8$ alkyl, or C(=O)-heterocyclic; and
----- is an optional double bond;
when one of R' or $R^3$ is O, then the other is not O,
when ---- is not present between ring carbons, $R^2$ is other than H;
$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl; and $R^8$ and $R^9$ are each independently selected from the group consisting of H, $C_1$-$C_8$ alkyl, $C_1$-$C_8$ alkoxy, amine, $C_1$-$C_8$ alkylamine, and halo;

with the proviso that when $R^2$ is 2-methyl propyl, $R^3$ is H, and ---- is not present, R' is not OH and is not O;

or an enantiomer, optical isomer, diastereomer, N-oxide, crystalline form, hydrate, or pharmaceutically acceptable salt thereof;

and a pharmaceutically acceptable carrier.

60. The pharmaceutical composition of claim 59 comprising a compound of formula IV:

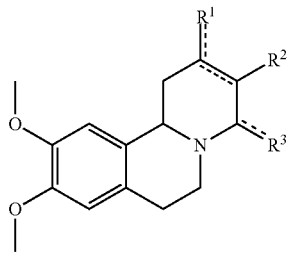

IV wherein $R^1$, $R^2$, and $R^3$ are as defined in claim 59;

X is NH or O; and $R^4$ is H, $C_1$-$C_8$ alkyl, —C(=O)-heterocyclic;

or an enantiomer, optical isomer, diastereomer, N-oxide, crystalline form, hydrate, or pharmaceutically acceptable salt thereof;

and a pharmaceutically acceptable carrier.

61. The pharmaceutical composition of claim 60 wherein the compound is selected from the group consisting of:

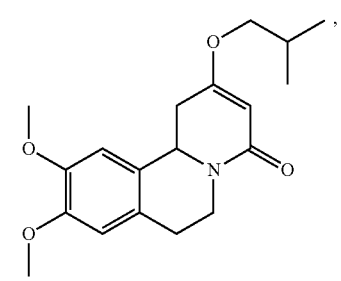

HG-8

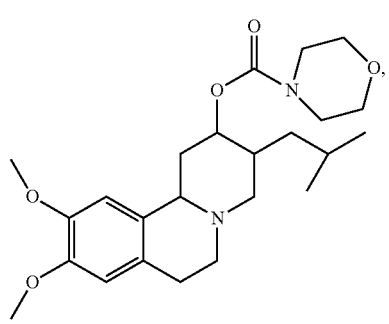

HG-11

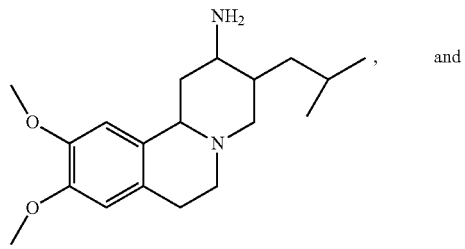

HG-6 and

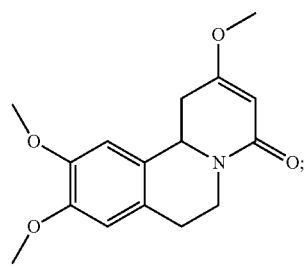

HG-10 or an enantiomer, optical isomer, diastereomer, N-oxide, crystalline form, hydrate, or pharmaceutically acceptable salt thereof;

and a pharmaceutically acceptable carrier.

62. A method of treatment or prevention of diabetes or hyperglycemia which comprises administering to a patient in need thereof an effective amount of a compound of formula III:

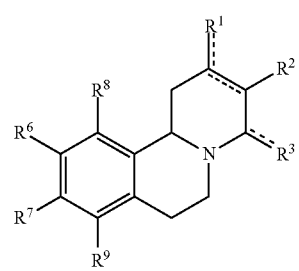

III wherein $R^1$ is $XR^4$ or O;

$R^2$ is H or $C_1$-$C_8$ alkyl;

$R^3$ is H or O;

X is O, S, NH or $CH_2$;

$R^4$ is H, $C_1$-$C_8$ alkyl, or C(=O)-heterocyclic; and

---- is an optional double bond;

when one of R' or $R^3$ is O, then the other is not O, when ---- is not present between ring carbons, $R^2$ is other than H;

$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl; and $R^8$ and $R^9$ are each independently selected from the group consisting of H, $C_1$-$C_8$ alkyl, $C_1$-$C_8$ alkoxy, amine, $C_1$-$C_8$ alkylamine, and halo;

with the proviso that when $R^2$ is 2-methyl propyl, $R^3$ is H, and ---- is not present, then R' is not OH and is not O;

or an enantiomer, optical isomer, diastereomer, N-oxide, crystalline form, hydrate, or pharmaceutically acceptable salt thereof.

63. A method of normalizing blood glucose levels which comprises administering to a subject in need thereof an effective amount of a compound of formula III:

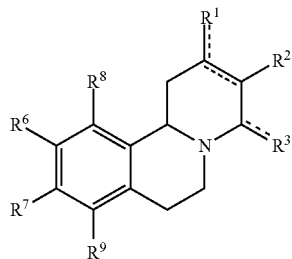

wherein
$R^1$ is $XR^4$ or O;
$R^2$ is H or $C_1$-$C_8$ alkyl;
$R^3$ is H or O;
X is O, S, NH or $CH_2$;
$R^4$ is H, $C_1$-$C_8$ alkyl, or C(=O)-heterocyclic; and
----- is an optional double bond;
when one of R' or $R^3$ is O, then the other is not O,
when ---- is not present between ring carbons, $R^2$ is other than H;
$R^6$ and $R^7$ are each independently selected from the group consisting of $C_1$-$C_8$ alkoxy, amine, $C_1$-$C_8$ alkylamine, halo, and 5- to 8-membered heteroaryl, wherein the 5- to 8-membered heteroaryl is optionally substituted with $C_1$-$C_8$ alkoxy, amine, $C_1$-$C_8$ alkylamine, halo, and 5- to 8-membered heteroaryl; and
$R^8$ and $R^9$ are each independently selected from the group consisting of H, $C_1$-$C_8$ alkyl, $C_1$-$C_8$ alkoxy, amine, $C_1$-$C_8$ alkylamine, and halo;
with the proviso that when $R^2$ is 2-methyl propyl, $R^3$ is H, and ---- is not present, then R' is not OH and is not O;
or an enantiomer, optical isomer, diastereomer, N-oxide, crystalline form, hydrate, or pharmaceutically acceptable salt thereof.

64. The method of claim 62 or 63 wherein the administering is of a compound of formula IV:

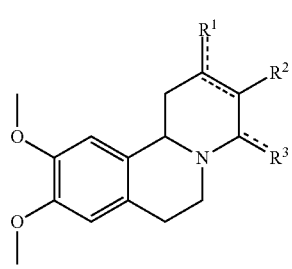

wherein
$R^1$, $R^2$, and $R^3$ are as defined in claim 58;
X is NH or O; and
$R^4$ is H, $C_1$-$C_8$ alkyl, —C(=O)-heterocyclic;
or an enantiomer, optical isomer, diastereomer, N-oxide, crystalline form, hydrate, or pharmaceutically acceptable salt thereof.

65. The method of claim 64 wherein the administering is of a compound selected from the group consisting of:

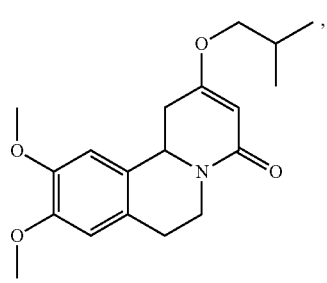

HG-8

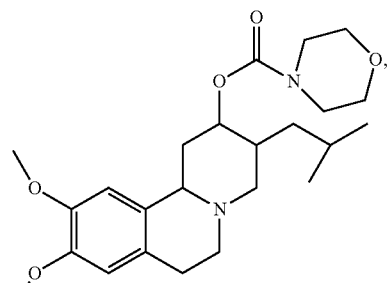

HG-11

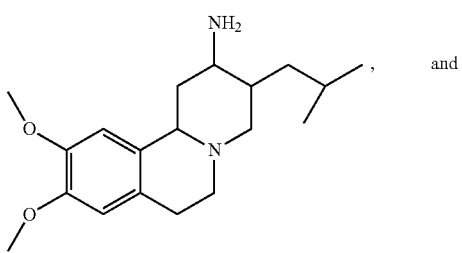

HG-6 and

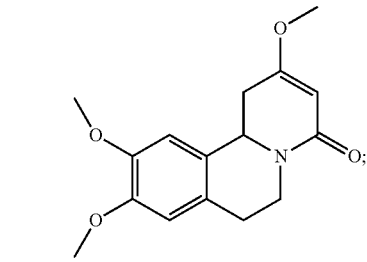

HG-10 or an enantiomer, optical isomer, diastereomer, N-oxide, crystalline form, hydrate, or pharmaceutically acceptable salt thereof.

* * * * *